US012773144B2

(12) United States Patent
Azuma et al.

(10) Patent No.: US 12,773,144 B2
(45) Date of Patent: Oct. 27, 2026

(54) INFORMATION PROCESSING SYSTEM, INFORMATION PROCESSING METHOD AND COMPUTER PROGRAM PRODUCT

(71) Applicant: Sony Group Corporation, Tokyo (JP)

(72) Inventors: Taro Azuma, Kanagawa (JP); David Duffy, London (GB); Christopher Wright, London (GB); Nicholas Walker, London (GB)

(73) Assignee: Sony Group Corporation, Tokyo (JP)

( * ) Notice: Subject to any disclaimer, the term of this patent is extended or adjusted under 35 U.S.C. 154(b) by 221 days.

(21) Appl. No.: 18/686,969

(22) PCT Filed: Jun. 28, 2022

(86) PCT No.: PCT/JP2022/025676

§ 371 (c)(1),
(2) Date: Feb. 27, 2024

(87) PCT Pub. No.: WO2023/037714

PCT Pub. Date: Mar. 16, 2023

(65) Prior Publication Data

US 2024/0382125 A1 Nov. 21, 2024

(30) Foreign Application Priority Data

Sep. 10, 2021 (EP) ..................................... 21196025

(51) Int. Cl.
*A61B 5/16* (2006.01)
*A61B 5/01* (2006.01)
(Continued)

(52) U.S. Cl.
CPC ................ *A61B 5/165* (2013.01); *A61B 5/01* (2013.01); *A61B 5/024* (2013.01); *A61B 5/026* (2013.01);
(Continued)

(58) Field of Classification Search
CPC ........... A61B 5/01; A61B 5/024; A61B 5/026; A61B 5/0531; A61B 5/0533; A61B 5/163;
(Continued)

(56) References Cited

U.S. PATENT DOCUMENTS

2004/0101178 A1 5/2004 Fedorovskaya et al.
2016/0262608 A1 9/2016 Krueger
(Continued)

OTHER PUBLICATIONS

International Search Report and Written Opinion mailed Nov. 2, 2022 in connection with International Application No. PCT/JP2022/025676.

*Primary Examiner* — Amanda K Hulbert
(74) *Attorney, Agent, or Firm* — Wolf, Greenfield & Sacks, P.C.

(57) ABSTRACT

An information processing system, the information processing apparatus comprising circuitry configured to: control a display device to display a first image to a user; detect a gaze location of the user corresponding to a portion of the first image observed by the user; acquire one or more content properties of the first image displayed to the user based on an analysis of the first image; acquire user response data relating to the user's autonomic response to the display of the first image; and determine a state of the user's mental condition based on the user response data, the one or more content properties of the first image and the gaze location of the user, wherein the mental condition includes at least one of anxiety and/or depression.

27 Claims, 10 Drawing Sheets

(51) Int. Cl.

| | |
|---|---|
| ***A61B 5/024*** | (2006.01) |
| ***A61B 5/026*** | (2006.01) |
| ***A61B 5/0531*** | (2021.01) |
| ***G06T 19/00*** | (2011.01) |
| ***G06V 10/56*** | (2022.01) |
| ***G06V 10/60*** | (2022.01) |
| ***G06V 40/16*** | (2022.01) |

(52) U.S. Cl.
CPC ............ *A61B 5/0531* (2013.01); *A61B 5/163* (2017.08); *G06T 19/006* (2013.01); *G06V 10/56* (2022.01); *G06V 10/60* (2022.01); *G06V 40/174* (2022.01); *G06V 2201/07* (2022.01)

(58) Field of Classification Search
CPC ...... A61B 5/165; G06T 19/006; G06V 10/56; G06V 10/60; G06V 2201/07; G06V 40/174
See application file for complete search history.

(56) References Cited

U.S. PATENT DOCUMENTS

| | | | | |
|---|---|---|---|---|
| 2016/0379225 | A1 | 12/2016 | Rider et al. | |
| 2017/0290504 | A1 | 10/2017 | Khaderi et al. | |
| 2017/0323485 | A1 | 11/2017 | Samec et al. | |
| 2017/0365101 | A1* | 12/2017 | Samec .................. | A61B 5/163 |

* cited by examiner

INFORMATION PROCESSING SYSTEM, INFORMATION PROCESSING METHOD AND COMPUTER PROGRAM PRODUCT

CROSS-REFERENCE TO RELATED APPLICATIONS

This application claims the benefit under 35 U.S.C. § 371 as a U.S. National Stage Entry of International Application No. PCT/JP2022/025676, filed in the Japanese Patent Office as a Receiving Office on Jun. 28, 2022, which claims priority to European Patent Application Number 21196025.7, filed in the European Patent Office on Sep. 10, 2021, each of which is hereby incorporated by reference in its entirety.

TECHNICAL FIELD

The present invention relates to an information processing system, information processing method and computer program product.

BACKGROUND

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present invention.

In recent years, there has been an increase in the desire to find new ways to identify and measure a mental condition or mental state of a person.

Depression and anxiety are examples of a mental condition of a person. Levels of depression and anxiety in a person are difficult to assess. In particular, many ways of measuring levels of depression and anxiety in a person require significant effort on the part of the person being tested, which means that it can be difficult to encourage people to be tested. This means that a condition such as depression and/or anxiety may go undetected through lack of testing.

Moreover, it can be difficult to distinguish between mental conditions such as depression and/or anxiety as often these conditions present similar symptoms. Therefore, accurate and reliable identification and measurement of mental conditions such as depression and/or anxiety can be difficult to achieve.

Effects of medication on the symptoms of the user's mental condition can be difficult to assess. Therefore, even if the mental condition of the user can be identified, it can be difficult to ensure that effective treatment is provided to control any symptoms the user experiences as a result.

Finally, owing to difficulties in measuring and identifying a mental condition of a person, it can be challenging to provide a person with digital content which is appropriate for that person. Indeed, providing a person who is experiencing symptoms of a mental condition access to certain digital content can further exacerbate their symptoms.

It is an aim of the present disclosure to address this issues.

SUMMARY

A brief summary about the present disclosure is provided hereinafter to provide basic understanding related to certain aspects of the present disclosure.

In a first aspect of the disclosure, an information processing system is provided, the information processing apparatus comprising circuitry configured to: control a display device to display a first image to a user; detect a gaze location of the user corresponding to a portion of the first image observed by the user; acquire one or more content properties of the first image displayed to the user based on an analysis of the first image; acquire user response data relating to the user's autonomic response to the display of the first image; and determine a state of the user's mental condition based on the user response data, the one or more content properties of the first image and the gaze location of the user, wherein the mental condition includes at least one of anxiety and/or depression.

In another aspect of the disclosure, an information processing system is provided, the information processing apparatus comprising circuitry configured to: detect a gaze location of a user corresponding to a portion of an image observed by the user on a display device; acquire one or more content properties of the first image displayed to the user based on an analysis of the first image; acquire user response data relating to the user's autonomic response to the display of the image; and determine a state of the user's mental condition based on the user response data, the one or more content properties of the image and the gaze location of the user, wherein the mental condition includes at least one of anxiety and/or depression.

In another aspect of the disclosure, an information processing system is provided, the information processing apparatus comprising circuitry configured to: determine a state of a user's mental condition based on user response data relating to a user's autonomic response to display of an image, one or more content properties of the image and a gaze location of the user corresponding to a portion of the image observed by the user; and generate a second image for display to the user, the second image being generated in accordance with the determined state of the user's mental condition.

In another aspect of the disclosure, an information processing system is provided, the information processing apparatus comprising circuitry configured to: control a display device to display an image to a user; detect a gaze location of the user corresponding to a portion of the image observed by the user; acquire one or more content properties of the first image displayed to the user based on an analysis of the first image; and acquire user response data relating to the user's autonomic response to the display of the image.

In another aspect of the disclosure, an information processing method is provided, the information processing method comprising: controlling a display device to display a first image to a user; detecting a gaze location of the user corresponding to a portion of the first image observed by the user; acquiring one or more content properties of the first image displayed to the user based on an analysis of the first image; acquiring user response data relating to the user's autonomic response to the display of the first image; and determining a state of the user's mental condition based on the user response data, the one or more content properties of the first image and the gaze location of the user, wherein the mental condition includes at least one of anxiety and/or depression.

In another aspect of the disclosure, an information processing method is provided, the information processing method comprising: detecting a gaze location of a user corresponding to a portion of an image observed by the user on a display device; acquiring one or more content properties of the first image displayed to the user based on an analysis of the first image; acquiring user response data relating to the user's autonomic response to the display of the image; and determining a state of the user's mental condition based on the user response data, the one or more content properties of the image and the gaze location of the user, wherein the mental condition includes at least one of anxiety and/or depression.

In another aspect of the disclosure, an information processing method is provided, the information processing method comprising: determining a state of a user's mental condition based on user response data relating to a user's autonomic response to display of an image, one or more content properties of the image and a gaze location of the user corresponding to a portion of the image observed by the user; and generating a second image for display to the user, the second image being generated in accordance with the determined state of the user's mental condition.

In another aspect of the disclosure, an information processing method is provided, the information processing method comprising: controlling a display device to display an image to a user; detecting a gaze location of the user corresponding to a portion of the image observed by the user; acquiring one or more content properties of the first image displayed to the user based on an analysis of the first image; and acquiring user response data relating to the user's autonomic response to the display of the image.

In another aspect of the disclosure, a computer program product is provided, the computer program product comprising instructions which, when implemented by a computer, cause the computer to perform a method of the present disclosure.

Further embodiments of the present disclosure are defined by the appended claims.

According to embodiments of the disclosure, a state of a mental condition of a user (i.e. any person) can be more accurately and reliably measured and identified. This can be achieved with minimally invasive techniques which thus makes it easier for the user to be tested. Moreover, according to embodiments of the disclosure, reliable differentiation of mental conditions of the user (such as anxiety or depression) can be readily achieved.

Of course, it will be appreciated that the present disclosure is not intended to be limited to these advantageous technical effects. Other technical effects will become apparent to the skilled person when reading the disclosure.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings.

DESCRIPTION OF EMBODIMENTS

Figure 1:
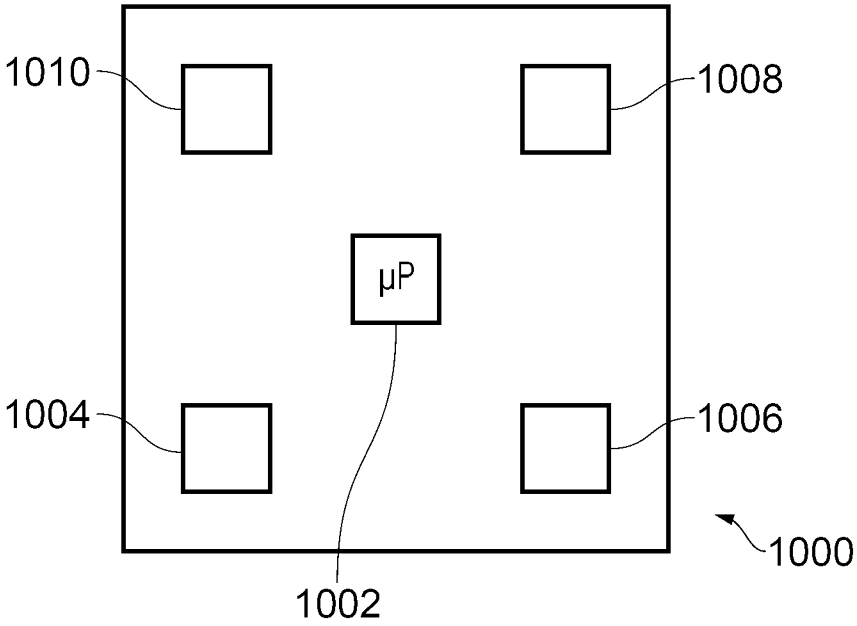
FIG. 1 illustrates an apparatus in accordance with embodiments of the disclosure.

Referring now to the drawings, wherein like reference numerals designate identical or corresponding parts throughout the several views.

Referring to FIG. 1, an apparatus 1000 according to embodiments of the disclosure is shown. Typically, an apparatus 1000 according to embodiments of the disclosure is a computer device such as a personal computer or a terminal connected to a server. Indeed, in embodiments, the apparatus may also be a server. The apparatus 1000 is controlled using a microprocessor or other processing circuitry 1002. In some examples, the apparatus 1000 may be a portable computing device such as a mobile phone, laptop computer or tablet computing device.

The processing circuitry 1002 may be a microprocessor carrying out computer instructions or may be an Application Specific Integrated Circuit. The computer instructions are stored on storage medium 1004 which maybe a magnetically readable medium, optically readable medium or solid state type circuitry. The storage medium 1004 may be integrated into the apparatus 1000 or may be separate to the apparatus 1000 and connected thereto using either a wired or wireless connection. The computer instructions may be embodied as computer software that contains computer readable code which, when loaded onto the processor circuitry 1002, configures the processor circuitry 1002 to perform a method according to embodiments of the disclosure.

Additionally, an optional user input device 1006 is shown connected to the processing circuitry 1002. The user input device 1006 may be a touch screen or may be a mouse or stylist type input device. The user input device 1006 may also be a keyboard or any combination of these devices.

A network connection 1008 may optionally be coupled to the processor circuitry 1002. The network connection 1008 may be a connection to a Local Area Network or a Wide Area Network such as the Internet or a Virtual Private Network or the like. The network connection 1008 may be connected to a server allowing the processor circuitry 1002 to communicate with another apparatus in order to obtain or provide relevant data. The network connection 1002 may be behind a firewall or some other form of network security.

Additionally, shown coupled to the processing circuitry 1002, is a display device 1010. The display device 1010, although shown integrated into the apparatus 1000, may additionally be separate to the apparatus 1000 and may be a monitor or some kind of device allowing the user to visualize the operation of the system. In addition, the display device 1010 may be a printer, projector or some other device allowing relevant information generated by the apparatus 1000 to be viewed by the user or by a third party.

As explained in the background, it is desired to find new ways to identify and measure a mental condition or mental state of a person.

Individuals suffering from anxiety have different autonomic responses to emotive stimuli appearing in central or peripheral vision. Moreover, for an individual suffering from anxiety, emotive stimuli presented in the peripheral vision causes a stronger autonomic response than an emotive stimuli presented in the central vision. On the other hand, an individual suffering from depression expresses both a reduced response to positive emotive visual stimuli, as well as stronger response to negative stimuli.

However, visual stimuli which have unknown properties cannot be used to characterize an individual's depression or anxiety symptoms. Moreover, methods of testing require significant effort on the part of the person being tested, which means that it can be difficult to encourage people to be tested. This means that a condition such as depression and/or anxiety may go undetected through lack of testing.

Accordingly, for at least these reasons (and those reasons explained in the Background) an apparatus (or system), method and computer program product are provided in accordance with embodiments of the disclosure.

Apparatus

Figure 2:
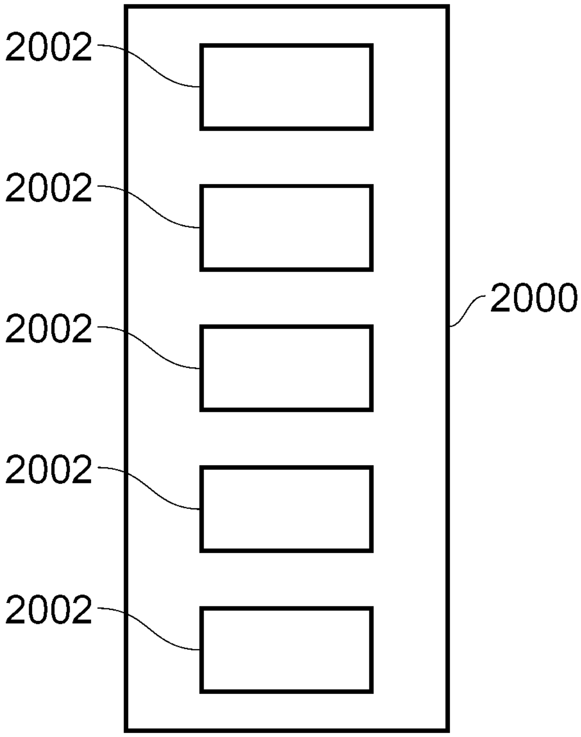
FIG. 2 illustrates an example configuration of processing circuitry of an apparatus according to embodiments of the disclosure.

FIG. 2 illustrates an example configuration of an apparatus (or system) 2000 in accordance with embodiments of the disclosure. Apparatus 2000 may be implemented as an apparatus such as apparatus 1000 described with reference to FIG. 1 of the present disclosure, for example. Apparatus 2000 comprises circuitry 2002 (such as processing circuitry 1002 described with reference to FIG. 1 of the present disclosure).

The circuitry 2002 of apparatus 2000 is configured to control a display device to display a first image to a user.

Then, the circuitry 2002 of apparatus 2000 is configured to detect a gaze location of the user corresponding to a portion of the first image observed by the user.

Once the gaze location of the user has been detected, the circuitry 2002 of apparatus 2000 is configured to acquire one or more content properties of the first image displayed to the user based on an analysis of the first image. In some, optional, examples, the circuitry of system 2000 may perform the analysis of the first image in order to acquire the one or more content properties. However, in other examples, the circuitry 2002 of system 2000 may acquire the result of an analysis which has been performed by an external entity or device in order to acquire the one or more content properties of the first image.

Furthermore, the circuitry 2002 of apparatus 2000 is configured to acquire user response data relating to the user's autonomic response to the display of the first image.

Finally, circuitry 2002 is configured to determine a state of the user's mental condition based on the user response data, the one or more content properties of the first image and the gaze location of the user, wherein the mental condition includes at least one of anxiety and/or depression.

In this manner, a mental condition of a user (i.e. any person) can be more accurately and reliably measured and identified.

Figure 3A:
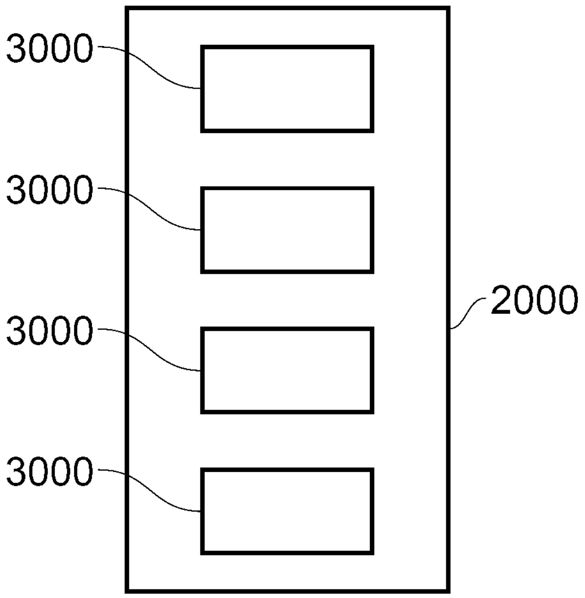
FIG. 3A illustrates an example configuration of an apparatus 2000 in accordance with embodiments of the disclosure.
Figure 3B:
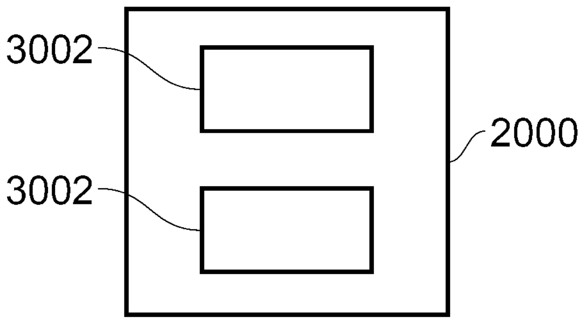
FIG. 3B illustrates an example configuration of an apparatus 2000 in accordance with embodiments of the disclosure.
Figure 3C:
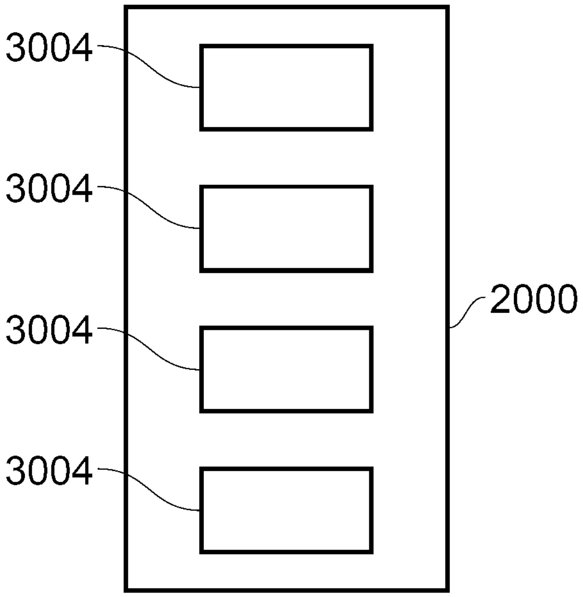
FIG. 3C illustrates an example configuration of an apparatus 2000 in accordance with embodiments of the disclosure.

However, apparatus 2000 may also be configured in accordance with the example of FIGS. 3A, 3B and 3C of the present disclosure. That is, each of FIGS. 3A, 3B and 3C illustrate an example configuration of an apparatus 2000 in accordance with embodiments of the disclosure.

As shown in FIG. 3A of the present disclosure, the circuitry 3000 of apparatus 2000 of the present disclosure may be configured to detect a gaze location of a user corresponding to a portion of an image observed by the user on a display device; acquire one or more content properties of the first image displayed to the user based on an analysis of the first image; acquire user response data relating to the user's autonomic response to the display of the image; and determine a state of the user's mental condition based on the user response data, the one or more content properties of the image and the gaze location of the user, wherein the mental condition includes at least one of anxiety and/or depression. This enables the state of the mental condition of the user to be determined even when apparatus 2000 does not control the display device.

As shown in FIG. 3B of the present disclosure, the circuitry 3002 of apparatus 2000 of the present disclosure may be configured to determine a state of a user's mental condition based on user response data relating to a user's autonomic response to display of an image, one or more content properties of the image and a gaze location of the user corresponding to a portion of the image observed by the user; and generate a second image for display to the user, the second image being generated in accordance with the determined state of the user's mental condition. This enables apparatus 2000 to determine the state of the mental condition of the user and adapt the content shown to the user in accordance with user response data received from a different, separate, device.

Finally, as shown in FIG. 3C of the present disclosure, the circuitry 3004 of apparatus 2000 of the present disclosure may be configured to control a display device to display an image to a user; detect a gaze location of the user corresponding to a portion of the image observed by the user; acquire one or more content properties of the first image displayed to the user based on an analysis of the first image; and acquire user response data relating to the user's autonomic response to the display of the image. This enables apparatus 2000 to acquire the user response data which can be passed to a different, separate, device for determination of the state of the mental condition of the user.

Embodiments of the disclosure, including apparatus 2000, will be described in more detail with reference to FIGS. 4 to 9 of the present disclosure.

Display of Image

As described with reference to FIG. 2 of the present disclosure, the circuitry 2002 of apparatus 2000 is configured to control a display device to display a first image to a user.

According to embodiments of the disclosure, the display device may consist of any display device which is suitable for displaying a first image to the user. In some examples, the display device may comprise a virtual reality display, an augmented reality display, a screen (such as a widescreen computer display) or the like. Moreover, in examples, the display device may be a display device such as display device 1010 as described with reference to FIG. 1 of the present disclosure. Therefore, in some examples, the display device may be internal to apparatus 2000, while in other examples, the display device may be external to apparatus 2000.

In order to be able to distinguish between different mental conditions of the user (e.g. between anxiety and depression) the display device which displays the first image (under control of apparatus 2000) should be configured such that it is capable of delivering visual stimuli in both peripheral and central regions of a user's vision. The display device may, in some examples, extend to a six degree angle from a central point of the user's vision. However, the present disclosure is not particularly limited in this regard, and the display device may extend to a different angle from the central point of the user's vision. Indeed, in some examples, a twelve degree angle from the user's central vision when measured from the user's viewing distance may be used. The range of the display may be much more or much less than these specific examples.

The circuitry 2002 of apparatus 2000 is configured to control the display device to display the image. In some examples, this may comprise generating a display signal which causes the display device to display the first image, for example. However, the present disclosure is not limited to this specific example.

The first image which is displayed to the user will vary in different examples of the disclosure. For example, the first image which is displayed may comprise content image data in the form of colour, intensity and location data (The "Image Data"). In other examples, the first image may be a single image or, alternatively, a collection of individual images (e.g. video).

The image to be displayed (i.e. the first image) may be obtained from an external storage or database (e.g. a content server or the like). That is, when apparatus 2000 is to be used to measure the mental condition of a user, apparatus 2000 may be configured to acquire the image from an external database (e.g. a content server or the like) using any wired or wireless communication link. Alternatively, said first image can be retrieved directly from the internal storage of apparatus 2000.

In the present disclosure, the content server is an external database or the like used to store visual media which may also include or not include an audio component, such as a TV show episode, YouTube video, game, still image or the like. Content from the database may be accessible to the user for downloading and viewing on the display device (i.e. as the first image). Moreover, in some examples, the user may be able to stream content for display directly from the server in a substantially real time environment.

Advantageously, according to embodiments of the disclosure, apparatus 2000 is configured to analyse the first image in order to determine one or more content properties of the first image. Therefore, the first image is not particularly limited in this regard (e.g. to any specific image or image content) and any image may be used as the first image depending on the situation. Accordingly, flexibility in using apparatus 2000 to measure and identify the mental condition of the user can be greatly increased.

In this manner, apparatus 2002 is configured to control a display device in order to display a first image to the user.

Gaze Location

As described with reference to FIG. 2 of the present disclosure, once the first image has been displayed to the user, the circuitry 2002 of apparatus 2000 is configured to detect a gaze location of the user corresponding to a portion of the first image observed by the user.

In some examples, the circuitry 2002 of apparatus 2000 may calculate gaze location data of the user (i.e. any person using apparatus 2000) by measuring the angle of the user's eyeball in x and y dimensions with respect to the gaze detection circuitry using a standard gaze direction estimation algorithm which is known in the art. For example this may be performed by standard pupil edge detection algorithms, where the position of the centre of the pupil is defined mathematically and then tracked over time. The gaze location may then be calculated from the gaze location data using a pre-defined function, unique to each display device, which converts the gaze angle to attended screen location.

In other words, the circuitry 2002 is configured to determine the user's gaze location within the spatial coordinates of the first image being displayed by the display device from gaze location data of the user and known functions of the display device. That is, given known properties of the display device (i.e. the distance and curvature of the screen), the corresponding angles with respect to locations relative to the viewed location can be determined by apparatus 2000.

The gaze detection circuitry (which measures the angle of the user's eyeball, for example) may consist of one or more image capture devices (e.g. self-facing cameras) which are configured to capture an image of the user's face and eyes. This enables the angle of the user's eyeballs relative to their face and/or the display apparatus to be measured, for example. In some examples, the one or more image capture devices may be included or mounted within a head mounted display. However, in other examples, said image capture devices may be configured in a location proximate to the display device.

The gaze detection circuitry is not limited to one or more image capture devices of this specific example. Rather, any other circuitry capable of detecting the gaze location of the user in the first image can be used in accordance with embodiments of the disclosure.

For example, thermally sensitive system such as a contact thermometer or thermal camera (where the output consists of temperature values over time) and/or depth or time of flight sensing systems which are able to output a depth map that can be used to identify facial expressions can also be used in order to determine to facial expressions and gaze direction of the user.

Accordingly, in some embodiments, the circuitry 2002 is further configured to detect a gaze location of the user using an eye tracking device.

Any suitable gaze detection circuitry which is able to detect the gaze direction of the user can be used in accordance with embodiments of the disclosure as required.

In this manner, circuitry 2002 of apparatus 2000 is configured to detect the gaze direction of the user.

Content Properties

Apparatus 2000 is configured to acquire one or more content properties of the first image displayed to the user based on an analysis of the first image.

In some, optional, examples, the circuitry of system 2000 may perform the analysis of the first image in order to acquire the one or more content properties. However, in other examples, the circuitry 2002 of system 2000 may acquire the result of an analysis which has been performed by an external entity or device in order to acquire the one or more content properties of the first image. The result of an analysis which has been performed by an external entity or device may be acquired from a storage device or database, for example. However, alternatively, the result of an analysis which has been performed may be acquired from the external entity or device using any suitable wired or wireless connection.

As explained above, the apparatus 2000 is configured to control a display device to display a first image to a user. This first image may, in some examples, have been acquired from a content server. In fact, in some examples, the first image may correspond to a certain digital content which the user wishes to view. As such, the content properties of the first image (such as the type of visual stimuli which are present within the first image) may be unknown. As such, if the user's response to the display of the first image is to be assessed in order to measure the mental condition of the user, it is necessary to determine the content properties of the image (e.g. determine the magnitude and location of the visual stimuli within the image).

Therefore, in some examples of the present disclosure, the one or more content properties of the first image includes the location of emotional stimuli within the first image.

As such, in some examples, apparatus 2000 may be configured to determine one or more content properties of the first image displayed to the user by determining properties of visual stimuli occurring within the first image (i.e. the image data). In examples, this may include determining, by circuitry 2002 of apparatus 2000, the existence of emotionally salient stimuli within the image data, where an object recognition technique is used to identify spatial sections of image data which contain stimuli with saliency properties. Emotionally salient stimuli are stimuli within the image which would cause an emotional response from the user. In examples, this may be an object or feature within the image which will cause a negative emotionally response from the user (e.g. scare the user or make the user sad) or will cause a positive emotional response from the user (e.g. relax the user or make the user happy).

Emotionally salient stimuli within the image can be identified by any suitable object recognition technique. In examples, this may be a standard object recognition approach which is known in the art, and which outputs a subsection of the image containing the stimuli, such as a rectangular bounding box.

Emotional properties of the emotionally salient stimuli may at least consist of a binary identifier for positive and negative emotional valence. Example emotionally salient stimuli with positive and negative emotional valence are shown in FIG. 4 of the present disclosure.

Figure 4:
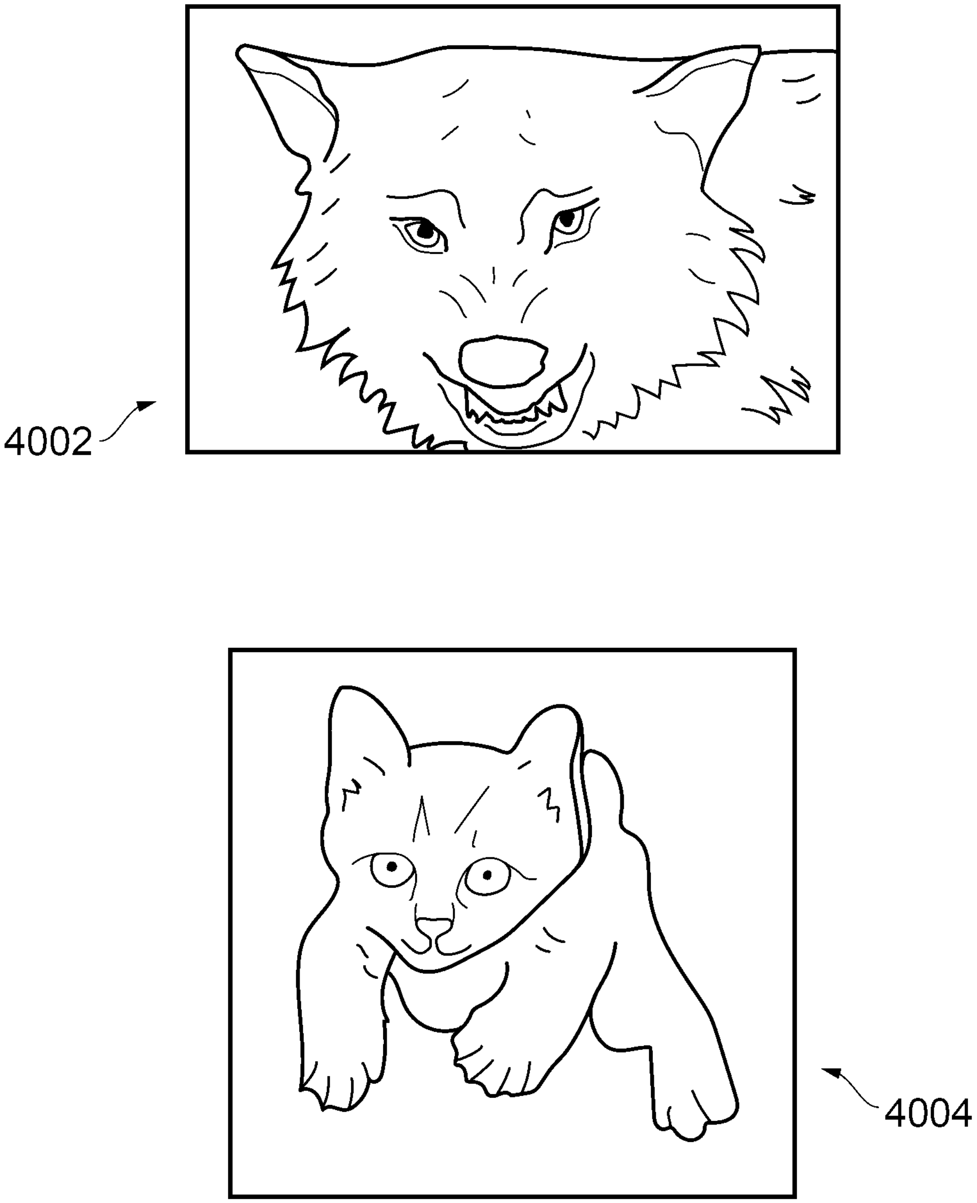
FIG. 4 illustrates an example of content properties in accordance with embodiments of the disclosure.

That is, FIG. 4 of the present disclosures illustrates an example of image content properties (such as emotionally salient stimuli) in accordance with embodiments of the disclosure.

In this example, an image (the first image) is illustrated. This image may be displayed to the user on a display device. Moreover, the image may have been retrieved from a content server, for example.

Within image, examples of visual stimuli (emotionally salient stimuli) which cause an emotional response from the user are illustrated.

The first visual stimulus is a negative stimulus 4002. A negative stimulus may be a visual object or feature which elicits a certain negative emotional response from the user. In the example illustrated in FIG. 4 of the present disclosure, the negative stimulus 4002 is a scary image of a wolf. This will cause an emotional fear response in the user.

The second visual stimulus is a positive stimuli 4004. This is a stimulus which causes a positive emotional response from the user. In the example illustrated in FIG. 4 of the present disclosure, the positive stimulus is a relaxing image of a kitten playing in a garden. This will relax the user and cause a positive emotional response.

Of course, it will be appreciated that the number of visual stimuli which are present in the first image is not particularly limited to the number illustrated in FIG. 4 of the present disclosure. The number of visual stimuli present in the first image data may be more than that illustrated in FIG. 4. Alternatively, the number of visual stimuli present in the first image data may be less than that illustrated in FIG. 4 of the present disclosure.

Moreover, the type of visual stimuli (such as objects or features within the image) are not limited to the specific examples of the cat and the wolf illustrated with reference to FIG. 4 of the present disclosure.

According to embodiments of the disclosure, the circuitry 2002 of apparatus 2000 may be configured to perform object recognition to identify all objects or features within the image data. The circuitry 2002 may then compare the objects or features which have been identified within the image with a lookup-table of object associations in order to determine positive and negative emotional response values for the objects and features which have been identified. Indeed, in some examples, a standard object recognition technique may be used to identify the location of emotionally salient stimuli within the image data. The object recognition may be pre-trained to recognize objects which have known emotional properties, such as a rainbow, or raincloud.

In other examples, a machine learning system may be used to identify the content properties of the image. The machine learning system may be trained on multiple training images to identify one or more content properties of the image based on inputs such as colour and brightness values of the image as well as recognized objects and scene properties.

In some examples, emotional image properties may be defined by a trained model (such as an AI system) or the like. Image analysis algorithms may recognize scene context factors, such as the environment context (indoors, outdoors, school, sport, driving etc.). This may consist of a pre-trained machine learning algorithm. The emotionally salient stimuli object or event can then be recognized in the image. Moreover, factors such as the average colour, contrast and light intensity values of the emotionally salient stimuli in the image can also be computed. These factors may be input into a pre-trained machine learning model which has been trained on image data with emotionally salient stimuli with labelled emotional image properties. In this manner, the content properties of the image can be determined by a trained model.

More specifically, once trained, the machine learning system is able to recognize and categorize objects within images, as well as recognize and categorize the context or background of the image. The high level features such as context and object are combined with low level information such as contrast and colour values. These features are used as inputs into a neural network which is trained on labelled image data, where the labels and output consist of both valence (positive or negative emotion) and arousal (boring or exiting image) values.

Alternatively, in other examples, apparatus 2000 may use a crowdsourcing system to determine the one or more content properties of the image. That is, emotional response data of other users who have previously viewed the image may be used in order to determine the content properties of the image.

In some examples, the one or more content properties of the image define different levels of positive or negative emotional valence (including stimulus intensities or general visual salience).

Alternatively, in some examples, where user physiological response data, consisting of physiological reactions with emotional valence, such as facial expressions, and corresponding emotionally salient stimuli are stored in a database located on the content server, the emotional image properties may instead be defined by the average response of the users to the image. That is, positive or negative emotional valence may be assigned to emotionally salient stimuli which elicit a corresponding detectable positive or negative physiological response in a pre-defined threshold proportion of viewers (such as 60%, for example).

Accordingly, by analyzing the first image data (or by acquiring the result of an analysis performed on the first image data), the apparatus 2000 is able to determine one or more content properties of the first image data (i.e. the image data which is displayed to the user). Therefore, the apparatus 2000 can identify within the image data a feature or set of features which will elicit a certain response (positive or negative) from the user. This enables the response of the user to the display of the image to be analyzed in order to determine or measure the mental state of the user. As explained in the Background, visual stimuli which have unknown properties cannot be used to characterize an individual's mental condition (such as depression or anxiety symptoms). However, since the apparatus 2000 is able to analyze the first image data in order to identify the content properties of the image, it is possible that any image data can be shown to the user for the purpose of measuring the mental condition of the user. This improves flexibility in measurement of a mental condition of the user and decreases the burden on the user. Moreover, since the user can undergo a test of mental condition using any content (e.g. content from the content server) it is possible to measure the mental condition of the user more frequently thus further improving the reliability of the measurement of the mental condition of that user.

User Response Data

As described with reference to FIG. 2 of the present disclosure, the circuitry 2002 of apparatus 2000 is configured to acquire user response data relating to the user's autonomic response to the display of the first image.

As explained, a user's response to the display of visual stimuli (such as the first image) can be used in order to determine the mental condition of the user.

Individuals suffering from a mental condition (such as anxiety) have different autonomic responses to emotive stimuli appearing in central or peripheral vision than a person who is not suffering from that mental condition. Moreover, for an individual suffering from anxiety, emotive stimuli presented in the peripheral vision cause a stronger autonomic response than emotive stimuli presented in the central vision. On the other hand, an individual suffering from depression (as a further example of a mental condition) expresses both a reduced response to positive emotive visual stimuli, as well as stronger response to negative stimuli.

As such, the circuitry 2002 of apparatus 2000 is configured to acquire user response data (being data relating to the user's autonomic response to the display of the first image).

In the present disclosure, the autonomic response of the user includes reflex actions of the autonomic nervous system of the user. These reflex actions include dilation of the pupils of the user's eyes, increase or decrease in the user's pulse or heart rate, increase or decrease in skin conductance (e.g. as a result of sweating), increase or decrease in blood pressure, transient changes in facial expressions or the like. Any reflex action of the autonomic nervous system of the user in response to the display of the first image can be acquired as the autonomic response of the user in accordance with embodiments of the disclosure.

The circuitry 2002 of apparatus 2000 may be configured to acquire the user response data in a number of different ways (depending, for example, on the nature of the autonomic response being measured).

Apparatus 2002 may be configured to monitor a change in the dilation of the user's eyes using one or more self-facing image capture devices. Accordingly, in some examples, the circuitry 2002 of apparatus 2000 may comprise a self-facing camera contained within a head mounted display, or mounted near to a computer monitor.

When measuring the dilation of the user's pupils, circuitry 2002 of apparatus 2000 may be configured to detect the pupil edges using a standard circular edge detection approach. This enables the edge of the pupil to be detected from an image of the pupil which has been acquired (e.g. from the self-facing image capture devices). Then, circuitry 2002 of apparatus 2000 is configured to calculate the diameter of the detected circle in terms of pixel distance in the recorded image data. Once the diameter of the circle (e.g. the pupil) has been detected, the circuitry 2002 is configured to measure changes in this diameter which occur over time, expressed as a proportion of the originally recorded value. This analysis may be performed continuously. Alternatively, upon detection of a visually salient stimuli in the first image (i.e. the content viewed by the user) a time series of this physiological response data (user response date) corresponding to a duration of time after stimulus presentation is recorded.

Of course, it will be appreciated that the present disclosure is not limited to this specific example and other ways of determining the dilation of the pupil of the user's eye can be performed as required depending on the situation.

The self-facing cameras contained within a head mounted display (or other self-facing image capture devices) used in order to determine the dilation of the user's pupils can also be used in order to determine pupillary saccadic motion as an autonomic response of the user. Standard pattern recognition algorithms may be used to detect these saccadic movements of the user's eyes. Furthermore, these pattern recognition algorithms may be used to detect small oscillations (microsaccades) and record their timing and duration. Large scale saccades may also be detected and defined in terms of their direction relative to the emotionally salient stimuli location (e.g. towards or away from the stimulus). The direction of the saccades (e.g. towards or away from the stimulus) and/or the magnitude and frequency of these saccades can be used in order to determine the response of the user to the display of the first image (and the emotional salient stimuli which are located therein). Thus, the saccadic movements of the user's eyes can be used as user response data for determining the mental condition of the user.

Alternatively, or in addition, the circuitry 2002 of apparatus 2000 may further comprise a number of skin contacting electrodes, where the data collected consists of current and voltage between electrode pairs. This enables the level of sweating of the user to be determined as the autonomic response of the user, for example. In particular, in some examples a small voltage is applied across the electrodes (e.g. 0.5V). Skin conductance may then be calculated based on the conductance between the electrode pair (based on the current which flows between the electrode pair). This skin conductance can then be acquired as user response data to be used when determining the state of the user's mental condition in accordance with embodiments of the disclosure.

Alternatively, or in addition, thermally sensitive systems such as a contact thermometer or thermal camera, where the output consists of temperature values over time and/or blood flow sensors such as an optical PPG sensor which may output light intensity data over time can be used in order to acquire the user response data. This enables changes in the user's heart rate or blood pressure to be acquired. Furthermore, this enables the skin temperature of the user to be acquired. In some examples, where a thermal camera is provided, a segmentation step may be performed to restrict the thermal data to the face, or areas of the face which show a strong physiological response to emotional content, such as the checks. In this case a standard facial area recognition algorithm may be performed to segment the user's face. Image segments which are marked with the relevant facial areas which are pre-defined in a lookup table, such as the checks, upper lip and forehead, may be stored as physiological response data. This improves accuracy and reliability when using thermal imaging to determine the response of the user to the display of the first image.

Blood flow sensors (such as optical PPG sensors) provide light intensity values over time. A standard cardiovascular PGG pattern recognition algorithm may be applied to recognise a section of the varying light intensity values which represents a repeating part of the cardiac cycle, such as the dicrotic notch, for example. The frequency of the cycle may therefore be determined over time (e.g. heart rate). The degree of variation from an average inter-pulse interval may be calculated in the form of standard deviation (heart rate variability). By monitoring blood flow of the user, the user's emotional response to the display of the first image (and the emotionally salient stimulus contained therein) can be acquired. Such data can then be used in order to determine the state of the mental condition of the user.

The data acquired from the blood flow sensors and/or thermal cameras can then be acquired as user response date for the determination of the state of the mental condition of the user in accordance with embodiments of the disclosure.

In some examples depth or time of flight sensing systems which are able to output a depth map that can be used to identify facial expressions as the user response data. Facial expressions may include movement of the cheeks, eyebrows, lips or other facial muscle movements, for example. In some examples, facial expression data can be acquired from image capture devices (e.g. a self-facing camera which captures an image of the user's face). Facial expression recognition methods may be used to determine the facial expression of the user from these images. As a specific example, such a facial expression recognition method may include first tracking points on the skin (e.g. key anchor points such as the location of the corners of the user's mouth). Then, the method may comprise measuring deformation of the face by movement of the tracked points. These movement patterns can then be compared to a known data set of facial expressions in order to recognise specific facial expressions. In particular, specific facial expressions can be recognised by a combination of movements from multiple tracked points. In some examples, all facial expressions may be defined as positive, negative or neutral valence. Then, the facial response of the user following the display of the first image (and the emotionally salient stimuli which are located therein) can be used as user response data to determine the state of the mental condition of the user in accordance with embodiments of the disclosure.

Furthermore, in some examples, the circuitry 2002 of apparatus 2000 may be configured to determine the user's autonomic response to the emotionally salient stimuli through additional analysis of the data acquired from a monitoring device (e.g. a camera, sensor or the like). In some examples, a machine learning or rules-based system may be used to detect patterns which are known to be correlated with a body physiological response to stimulus. This enables the user response to the presentation of the first image data to be measured.

According to certain embodiments of the disclosure, data is acquired or recorded for a physiologically relevant period after the presentation first image. This may be a period such as 0 to 3 seconds afterward the first image has been displayed, for example. This ensures that data most relevant to the user's autonomic response to the display of the first image is recorded. However, the period is not limited in this regard, and a different period for acquiring and recording the data may be used as required. Moreover, in some examples, the data may be acquired and recorded continuously. Then, the data may be timestamped such that the data most relevant to the user's autonomic response to the presentation of the first image can be later retrieved.

While a number of different examples of user response data have been provided, it will be appreciated that the present disclosure is not particularly limited to these specific examples. Rather, any data which indicates the autonomic response of the user to the first image can be acquired as the user response data in accordance with embodiments of the disclosure as required. The type of data, and the manner of its acquisition, will vary in accordance with the situation to which the embodiments of the disclosure have been applied.

As such, circuitry 2002 is configured to acquire user response data in response to the display of the first image on the display device.

State of Mental Condition

As described with reference to FIG. 2 of the present disclosure, circuitry 2002 is configured to determine a state of the user's mental condition based on the user response data, the one or more content properties of the first image and the gaze location of the user. In embodiments of the disclosure, the mental condition of the user can include anxiety and/or depression, however the present disclosure is not particularly limited in this respect.

In the present disclosure, the mental condition of a user is a condition which is identifiable from the user's autonomic reaction to visual stimuli with different emotional valence and visual field position. In particular, the mental condition comprises depression, anxiety and stress, but the embodiments of the present disclosure can also be applied to other mental conditions as required. Accordingly, the present disclosure is not particularly limited in this regard.

In particular, individuals suffering from a mental condition such as anxiety have different autonomic responses to emotive stimuli appearing in central or peripheral vision, which can be used to separate diagnosis from other mental conditions such as depression. Specifically, for individuals with anxiety, emotive stimuli presented in the peripheral vision have a much stronger autonomic response (e.g. pupil dilation or the like) than those presented in their central vision. In contrast to anxiety and normal controls, individuals suffering from depression exhibit greater reactivity to negative/unpleasant stimuli in the central vision compared to peripheral vision.

In other words, differentiation between anxiety and depression symptoms can be achieved by presenting stimuli of different levels of emotion (unpleasant, neutral, pleasant) and different regions of vision (central vs peripheral), and monitoring the autonomic response (via pupil dilation, skin conductance, or heart rate).

Therefore, the response of the user to the display of the first image can be used in order to measure the mental condition of the user.

In some examples, the circuitry 2002 of apparatus 2000 may be trained before the apparatus may be implemented in a usage phase. The training method may proceed using a standard process with specific inputs.

A dataset may be compiled of physiological response data and visual stimulus properties for users with certain predetermined mental conditions, where ground truth mental condition data may exist for these users in the form of condition severity scores assigned by medical professionals. Optionally, these may also be in the form of numeric values between 0-1 as a rating of the severity of the mental condition of the user (e.g. how likely the user is to experience symptoms as a result of their mental condition). The dataset may also include control users who are known to have approximately 0 scores for the mental conditions. This allows for reliable comparison with data from individuals who do not experience the mental condition. Furthermore, the dataset may also include a time-series of physiological response data and visual stimulus properties for each user, for example relating to a month leading up to the ground truth diagnosis.

The training dataset may be split into a training set and a test set. In examples, approximately 80% of the cases may be used in the training set. The circuitry 2002 may then be initialized with random weights. For each case in the training set, a prediction of the mental condition data is made and a score is created based on the average deviation from the target ground truth mental condition data.

Then, adjustments are made to the node weights and the process is repeated. These adjustments may be calculated by apparatus 2000 based on a multi-dimensional solution space exploration and optimization approach such as a Monte Carlo process.

Once a pre-set number of cycles has completed, or the success score has reached a threshold value, the trained model may then be run on the test set, and the success score for this set is used as the performance metric. Once validated (i.e. when the performance metric is higher than a predetermined threshold) the model can then be used on actual data in order to determine the mental condition of the user.

Importantly, the state of the mental condition is measured based on the user response data, the one or more content properties of the first image and the gaze location of the user.

Figure 5:
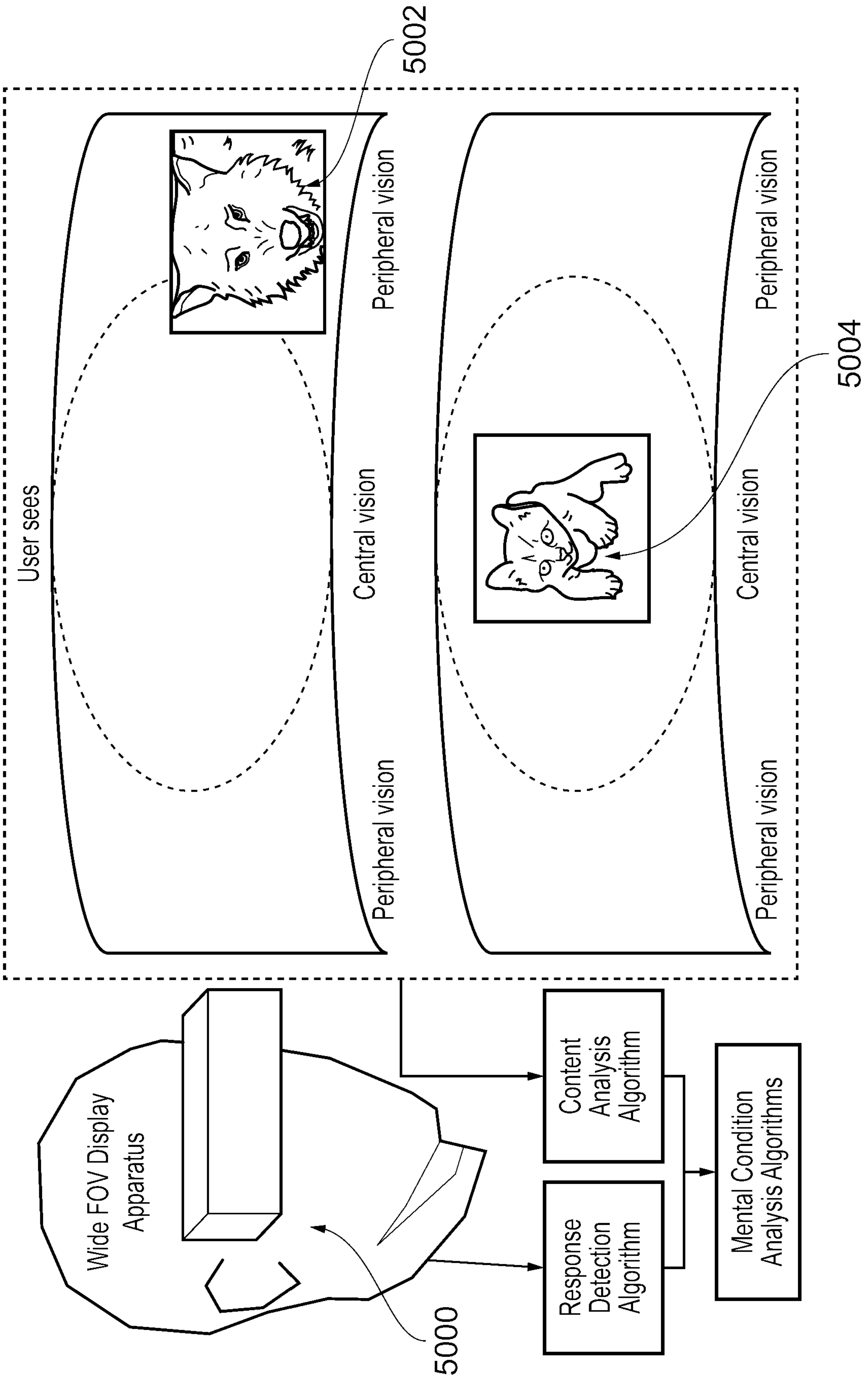
FIG. 5 illustrates an example situation in accordance with embodiments of the disclosure.

Consider, now, the example of FIG. 5 of the present disclosure. In this example, a user 5000 is wearing a wearable display device (such as a head-mounted display). Images are displayed to the user on the wearable display device.

For each image which is displayed to the user, apparatus 2000 is configured to analyze the image in order to determine and identify visual stimuli in the images.

At a first stage, an object 5002 is shown to the user, as part of the images displayed to the user. Apparatus 2000 determines this object 5002 is a visual stimulus which causes a negative emotional response in the user. That is, in this specific example, the object 5002 is an image of a wolf. The appearance of such an object is known to elicit a negative fear response in the user.

Accordingly, at this stage, the circuitry 2002 of apparatus 2000 can acquire user response data which indicates how the user has responded to the display of object 5002. That is, as described above, circuitry 2002 can acquire data indicative of the autonomic response of the user. In this specific example, the autonomic response of the user is the dilation of the user's pupils in response to the display of object 5002. The diameter of the user's pupils (and thus the level of pupil dilation) can be acquired by a self-facing camera incorporated in the wearable display device, for example.

Furthermore, at this time, circuitry 2002 of apparatus 2000 can further determine where in the field of view of the user the object 5002 appears. This is determined by determining the gaze location of the user. In this example, the gaze location of the user can be determined using eye-tracking techniques with image data from the self-facing camera incorporated in the wearable display device.

In this example, it is determined by apparatus 2000 that the object 5002 appears in the peripheral vision of the user.

Hence, apparatus 2000 is able to acquire information regarding the negative visual stimuli which have been displayed to the user (i.e. the one or more content properties of the image), information regarding where the negative visual stimuli appear in the field of vision of the user (i.e. the gaze direction of the user), and information regarding how the user responds to the appearance of the negative visual stimuli (i.e. the user response data).

Now, at a later stage, a further image is shown to the user 5000. This further image is an image which comprises an object 5004. In this specific example, the object 5004 is an object of a kitten.

Apparatus 2000 analyses the images which has been displayed to the user (i.e. the further image) and identifies that positive visual stimuli (object 5004) are present. The appearance of such an object is known to elicit a positive emotional response in the user.

The circuitry 2002 of apparatus 2000 can acquire user response data which indicates how the user has responded to the display of object 5004. That is, as described above, circuitry 2002 can acquire data indicative of the autonomic response of the user. In this specific example, the autonomic response of the user is the dilation of the user's pupils in response to the display of object 5002. The diameter of the user's pupils (and thus the level of pupil dilation) can be acquired by a self-facing camera incorporated in the wearable display device, for example.

Furthermore, at this time, circuitry 2002 of apparatus 2000 can further determine where in the field of view of the user the object 5004 appears. This is determined by determining the gaze location of the user. In this example, the gaze location of the user can be determined using eye-tracking techniques with image data from the self-facing camera incorporated in the wearable display device.

In this example, it is determined by apparatus 2000 that the object 5004 appears in the central vision of the user.

Hence, apparatus 2000 is able to acquire information regarding the positive visual stimuli which have been displayed to the user (i.e. the one or more content properties of the image), information regarding where the positive visual stimuli appears in the field of vision of the user (i.e. the gaze direction of the user), and information regarding how the user responds to the appearance of the positive visual stimuli (i.e. the user response data).

Once the information for the negative visual stimuli (e.g. the image of the wolf) and the positive visual stimuli (e.g. the image of the kitten) has been acquired, apparatus 2000 can measure the mental condition of the user.

In some examples, the mental condition of the user can be measured using the trained model (i.e. the model trained on the training data sets). That is, the trained model can be run on the data which has been acquired in order to determine the mental condition of the user. Specifically, the circuitry 2002 of apparatus 2000 may calculate the user's mental condition by inputting the user response data, gaze direction and content properties into the trained model whereby functions are applied to the data based on the weights and models which exist within the trained neural network. Then, the trained model will output the mental condition of the user which has been measured. Optionally, historic user response data may also be used as an input, such that changes over time may also be used for measurement of the mental condition of the user.

In other examples, a direct comparison can be made between the strength of the user's autonomic response to the display of the visual stimuli with that of other users (a control sample) for the given visual stimuli and the location of that visual stimuli in the field of view of the user. For example, if the user responds very strongly to visual stimuli in the peripheral vision but less strongly to the visual stimuli in the central vision then it can be determined that the user is suffering from anxiety. Alternatively, if the response of the user to the negative stimuli is very strong then it can be determined that the user may be suffering from depression.

In some examples, a rules based analysis may be performed by apparatus 2000 in order to determine the mental condition of the user.

Specifically, for a mental condition of depression, predefined threshold values for 'normal' and 'depressed' states for the physiological response data for a particular emotionally salient stimulus can be established. For example, this value may be defined by an expert through an initial testing procedure. Threshold values may include autonomic responses which are significantly higher for negative stimuli than positive or neutral; autonomic responses which are lower for positive stimuli than expected for a normal person; and autonomic responses which are triggered more significantly by stimuli in the central vision rather than the peripheral vision.

Accordingly, if the current user exhibits values that are below this threshold, a positive predictive score of 1 may be returned for the Mental Condition Data. Over many examples of emotionally salient stimuli, an average score may be calculated. Several pre-defined thresholds may be applied for this average score to determine if the user is in an 'normal, 'at risk' or 'depression' band. The threshold values may alternatively be defined as an amplitude of change in physiological response data for a given emotionally salient stimulus.

For example, for pupil dilation responses, this may be defined as a statistically significant 5% reduction in response amplitude over the period of a month. However, it will be appreciated that the present disclosure is not particularly limited in this regard and the threshold level reductions required may be much higher and/or much lower than 5%. Moreover, they may be monitored over a much longer or much shorter period than one month depending on the situation.

Furthermore, a mental condition of anxiety may be detected by comparing the physiological response data (user response data) to negative or positive valence emotionally salient stimuli compared to neutral valence stimuli occurring at angles defined as the user's 'peripheral vision' (>12 degrees from the attended point, for example).

A positive anxiety result may be returned if the amplitude of the user's average response to negative or positive valence Emotionally Salient Stimuli in the peripheral vision is greater than the average response in the central vision (<12 degrees), and greater than the average response to neutral stimuli.

Again, this average may be taken as a moving average over a time period such as a week or month. However, the time periods may be much longer or much shorter than this depending on the example situation to which embodiments of the present disclosure are applied.

Furthermore, a differentiation between anxiety and depression conditions can be made specifically by comparing the user physiological response data to emotionally salient stimuli in peripheral versus central vision.

In particular, heart rate recovery time to return to baseline after presentation of emotionally salient stimuli has been shown to be a useful indicator. A greater reactivity to central visual negative stimulus indicates depression, and a greater reactivity to peripheral negative visual stimulus indicates anxiety. Depression with anxiety (a person with both conditions) are also expected to have a greater reactivity to peripheral negative visual stimulus.

Alternatively, differentiation between anxiety and depression conditions can be achieved by presenting negative valence emotionally salient stimuli to the user in central vision and presenting negative valence emotionally salient stimuli to the user in the peripheral vision. This must be presented in a separate instance when the user's autonomic state has returned to baseline. Then, apparatus 2000 can calculate a depression or anxiety indicator from the response data, where a greater response to the peripheral visual stimulus indicates anxiety, and the reverse indicates depression.

In some examples, a score may be assigned to a user for each of a number of mental conditions. Mental condition data may therefore consist of a value of the user's depression and anxiety scores, and score confidence values. These values may be expressed as values between 0 and 1. This improves the ability to characterize the severity of the user's mental condition and, furthermore, makes communication of the mental condition of the user to an end user (e.g. either the user themselves or a healthcare professional or the like) more efficient. In other words, this enables quantification of a user's current state of the mental condition which may be useful for detecting treatment effect and/or for other medical purposes.

Medical condition data may also consist of information of the effect of medications which the user is taking, of the user's stress level and/or of the user's focus and attention.

Optionally, a system may be provided to communicate the mental condition data to the user, or to other stakeholder such as health insurers or health practitioners. This may consist of standard communication apparatus and systems. In some examples, this may be a network connection such as network connection 1008 described with reference to FIG. 1 of the present disclosure.

Of course, while examples of the present disclosure have been described with reference to FIG. 5 of the present disclosure, it will be appreciated that the embodiments of the disclosure are not particularly limited to this example situation. For example, the type of visual stimuli which are presented to the user are not limited to the specific examples of object 5002 (the wolf) and object 5004 (the kitten).

Rather, any suitable visual stimuli which elicit an emotional response (e.g. an autonomic response) from the user can be used in accordance with embodiments of the disclosure. Indeed, the type of feature or features which are provided as visual stimuli may vary in accordance with the content which the user is viewing on the display device. Advantageously, any image data can be used in this regard, as the apparatus 2000 identifies such features within the image data and determines the content properties of the image on this basis.

Moreover, it will be appreciated that while two different objects (i.e. the image of the wolf and the image of the kitten) have been illustrated in the example of FIG. 5, the present disclosure is not limited in this regard. Indeed, the number of stimuli presented to the user may be less than this (e.g. a single visual stimulus) or, alternatively, may be considerably higher than this number. The number of said features which are presented to the user will again depend on the type of content which the user is viewing at the time when the mental condition of the user is assessed.

Hence, in some examples, circuitry 2002 of apparatus 2000 is further configured to use the location of the emotional stimuli within the first image and the gaze direction of the user to determine whether the emotional stimuli within the first image are within the central vision or peripheral vision of the user; and determine the state of the user's mental condition based on whether the emotional stimuli within the first image are within the central vision or peripheral vision of the user and the user response data.

Furthermore, in some examples, the circuitry 2002 is further configured to differentiate between a mental condition of anxiety and depression by comparing the user response data for emotional stimuli in the central vision and emotional stimuli in the peripheral vision of the user.

In this manner, the circuitry 2002 of apparatus 2000 is configured to determine the determine a state of the user's mental condition.

Method

Figure 6:
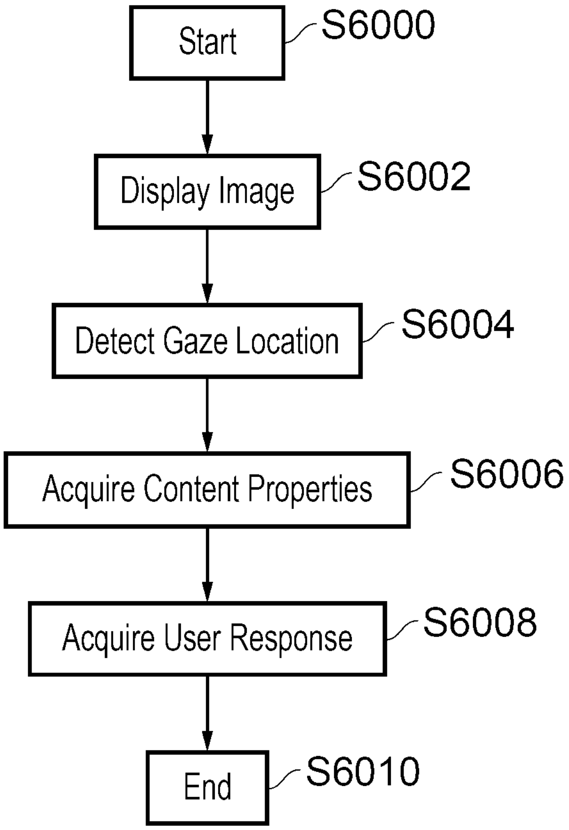
FIG. 6 illustrates a method in accordance with embodiments of the disclosure.

FIG. 6 illustrates a method in accordance with embodiments of the disclosure. The method of FIG. 6 may be implemented by an apparatus such as apparatus (or system) 2000, for example.

The method begins with step S6000 and proceeds to step S6002.

In step S6002, the method comprises controlling a display device to display a first image to a user.

Then, the method proceeds to step S6004.

In step S6004, the method comprises detecting a gaze location of the user corresponding to a portion of the first image observed by the user.

Then, once the gaze location of the user has been detected, the method comprises acquiring one or more content properties of the first image displayed to the user based on an analysis of the first image (step S6006).

The method then proceeds to step S6008.

In step S6008, the method comprises acquiring user response data relating to the user's autonomic response to the display of the first image.

In step S6010, the method comprises determining a state of the user's mental condition based on the user response data, the one or more content properties of the first image and the gaze location of the user, wherein the mental condition includes at least one of anxiety and/or depression.

Finally, the method proceeds to and ends with step S6012.

It will be appreciated that the method of the present disclosure is not particularly limited to the specific ordering of the steps of the method illustrated in FIG. 6 of the present disclosure. Indeed, in some examples, the steps of the method may be performed in an order different to that which is illustrated in FIG. 6. Moreover, in some examples, a number of steps of the method may be performed in parallel. This improves the computational efficiency of the method of determining a state of the user's mental condition.

Advantageous Technical Effects

According to embodiments of the disclosure, the state of the user's mental condition can be efficiently and reliably determined.

That is, according to embodiments of the disclosure, mental conditions of the user are determined using data relating to emotional properties of the image (i.e. content properties) visual field spatial properties of a stimulus (i.e. gaze direction of user compared to the stimulus) and the user's response to that stimulus (i.e. user response data). This enables the determination of mental condition to be achieved with minimally invasive techniques which thus make it easier for the user to be tested and a state of their mental condition to be determined. Moreover, according to embodiments of the disclosure, reliable differentiation of mental conditions of the user (such as anxiety or depression) can be readily achieved.

Of course, it will be appreciated that the present disclosure is not particularly limited to these advantageous technical effects. Other advantageous technical effects will become apparent to the skilled person when reading the disclosure.

Content Creation

Certain embodiments of the disclosure have been described with reference to the apparatus of FIG. 2 of the present disclosure and the method of FIG. 6 of the present disclosure. However, the present disclosure is not particularly limited in this regard, and a number of further additional modifications can, optionally, be made to these embodiments of the disclosure.

As explained with reference to FIG. 2 of the present disclosure, the first image which is acquired for display to the user may be content from a content server. Accordingly, the first image may comprise digital content such as a TV show episode, YouTube video, game, still image or the like (The "Content Items") in a database which may be accessible to the user for downloading and viewing.

Apparatus 2000 monitors the user's reaction to the first image (and the visual stimuli contained therein). This is used in order to determine the state of the mental condition of the user.

Accordingly, apparatus 2000 can determine how the content which is being displayed to the user is affecting the user. For example, if the state of the mental condition of the user shows that the user is exhibiting a high level of anxiety, it can be determined that the content is scaring the user and making them very anxious. On the other hand, if the state of the mental condition of the user shows that the user is experiencing depression, it can be determined that the content which is being displayed to the user is making the user unhappy.

Therefore, by monitoring changes in the mental condition of the user during the display of the content from the content server, apparatus 2000 can determine how the content is affecting the user.

In some examples, a content creation system can therefore be provided to create or adapt the delivery of content items (the "Adapted Content") to the user based on the user's mental condition. As such, if the content is affecting the mental condition of the user (e.g. making the user very sad) the content can be adapted to positively change the state of the mental condition of the user (e.g. by adapting the content such that features which make the user happy are included in the content).

Accordingly, in some embodiments of the disclosure, circuitry 2002 of apparatus 2000 is further configured to generate a second image for display to the user, the second image being generated in accordance with the determined state of the user's mental condition.

In some examples, the content creation system is configured to generate a personalized recommendation for content items for the user to consume. This system may consist of a database of user gaze location data for each content item on the content server. The content creation system is then configured to use a lookup table to determine the desirable visual stimulus properties for each mental condition. The content creation system then generates a score value of each content item based on the user's mental condition. As such, content items with a score over a certain threshold value can then be recommended to the user for consumption. For example, if the state of the mental condition of the user shows that the user is feeling scared, the content creation system may generate a list of recommended content items (e.g. images, videos or the like) which will relax the user and make them feel less scared.

In other examples, the content creation system can generate new content for the user to consume. That is, if the mental condition of the user is determined to be in a first state (such as feeling depressed), the content creation system may generate a new content item (such as an image) comprising a number of features which will improve the mental condition of the user (e.g. a number of sub-images of things that make the user happy). The content creation system may generate the new content based on predefined user preferences (e.g. a list of features which make the user happy).

Alternatively, in other examples, the content creation system may modify the content which is being displayed to the user. For example, the content creation system may identify features within the content which is being displayed to the user which have high emotional impact on the user (e.g. the emotionally salient stimuli in the image). Then, based on the state of the mental condition of the user, the content creation system may adapt the content which is being displayed to the user by removing one or more of the features in the content (e.g. by blocking out that portion of the image). In this manner, the content creation system may modify the content which is being displayed to the user in accordance with the state of the mental condition of the user in a way to positively improve the state of the mental condition of the user.

Therefore, in some examples, the circuitry 2002 of apparatus 2000 is further configured to adapt the first image by adapting the one or more content properties of the first image. Moreover, the circuitry 2002 is further configured to generate the second image for display to the user by adapting the first image in accordance with the determined state of the user's mental condition.

In some examples, the content creation system creates the adapted content (or recommended content list) by analyzing the content properties of the content being displayed to the user. Then, average or predicted user gaze locations may be retrieved from a database to define the gaze location data for the content items. Accordingly, it is possible to determine where the user is/will be looking when the content is displayed. Each item of content on the content server can then be scored using a lookup table of visual stimuli properties which provide value for the mental conditions which are relevant to the user's mental condition data.

As an example, for anxiety, this may be emotionally salient stimuli with positive/negative emotional valence which occur in the peripheral vision of the average user's visual field (e.g. 12 degrees from the average user's focal point, for example).

Alternatively, therefore, the circuitry 2002 is further configured to generate the second image data for display to the user by acquiring the second image data from a content server in accordance with the determined state of the user's mental condition.

Apparatus 2000 may then perform a matching operation to determine the number of emotionally salient stimuli which occur within each content item on the content server which can provide diagnostic value for the mental conditions of the user.

A separate summed number will be created for each mental condition. Apparatus 2000 may then be configured to take the inverse of the user's confidence scores in the mental condition data and multiple the inverse confidence by the summed number of emotionally salient stimuli in the content item. The content items which are presented to the user can then be ranked at least in part based on this value.

This enables a list of recommended content determined based on the determined state of the mental condition of the user to be provided.

Alternatively, the content creation system may modify the content by changing the location of emotionally salient stimuli in the image data to reduce the impact of those features on the mental condition of the user. Given the known visual stimuli properties which provide diagnostic value for the mental condition of the user, emotionally salient stimuli may be identified within the content items which match to all desired criteria apart from stimuli angle data or emotional image properties. Location of the emotionally salient stimuli may be modified by changing the position of the emotionally salient stimuli within the image data, for example to a point which is 12 degrees or more from the average gaze location. Stimuli may be selected which are likely to fall below a threshold of noticeability for the change, e.g. already occurring at 10 degrees from the average user attended location. An AI system may be implemented to achieve the movement of the Emotionally salient stimuli without creating unwanted image manipulation artifacts.

Emotional valence of the stimuli may be edited by an AI system such as a generative adversarial network. This AI system may be configured to add features to existing image data, such as party hats, fluffy cars, or other features which may be associated with negative or positive valence.

Alternatively, the AI system may be configured to manipulate image data, such as manipulating images of faces to create facial expressions which have a negative or positive valence.

Furthermore, where the content creation system may create new content, the new content may consist of new content items which can be created by generative algorithmic means. For example, this may be short content which is created such as Tik Tok videos, advertising content, or the like. Generative content algorithms may be trained with image data containing emotionally salient stimuli with pre-defined desired visual stimulus properties for diagnosis of mental conditions.

Alternatively, content items may be generated in the embodiment where the items are games. For example, elements may be introduced to the game environment which are likely to be in the user's central and peripheral vision during play. The functioning of this system may depend significantly on the game type and content and is therefore not particularly limited. For example, a first person shooter game with procedurally generated content may introduce reward content (positive emotional valence) and threat content (negative emotional valence) into portions of the visual field.

Apparatus 2000 may generate this content by selecting central, peripheral, positive and negative stimuli options such that over the duration of a game, roughly even numbers of stimuli are presented in each combination of categories, but presented in a random order such that the user cannot learn any pattern of presentation. More simple visual features, such as a user interface, where emotionally salient stimuli are introduced during user interaction with a system such as a menu system. For example, emotionally salient visual objects may be brought into view as features in a dynamic background scene.

Manually or automatically scrolling feeds, such as a social news feed, chat feed, or advertising feed may also be provided in accordance with the state of the mental condition of the user. For example, if a user is engaging with content near the bottom of the feed, new features can be introduced to their central visual field via the feed which have desired emotional image properties. Alternatively, if they are attending to content near the top of the feed, or attending to other windows of content, content items may be introduced to the user's peripheral visual field which have desired emotional image properties. For example in a video game streaming service, chat feeds are often displayed adjacent to the video game image stream. Emotionally salient stimuli may be introduced to the chat feeds at times when the user is looking at the feed or looking at the game.

However, the content creation system is not limited to these specific examples. Any method of content creation can be used as desired insofar as the content creation system generates or adapts the content provided to the user in accordance with the determined state of the mental condition of the user. Nevertheless, it will be appreciated that optimized content creation and recommendation systems allow the mental condition of the user to be performed more reliably, achieving higher accuracy over a shorter timescale than explicit content adjustment. Moreover, adapting the content through optimized content creation with the content creation system ensures that the content displayed to the user content which is most suitable for the user in accordance with their determined mental condition.

Treatment Effectiveness

In some examples, the circuitry 2002 of apparatus 2000 may additionally determine the effectiveness of treatments which affect mental conditions of the user.

That is, in some examples, the apparatus 2000 may store the determined state of the mental condition of the user in a database or storage device as mental condition data.

Then, the circuitry 2002 of apparatus 2000 may be configured to analyze a time series of mental condition data, together with known times and dosages of a treatment plan. For example, the dosage data may be input manually, communicated from a smart pill delivery device, or may be retrieved from a treatment schedule. Changes in mental condition data may be compared against pre-defined thresholds for treatment effectiveness to define results such as 'no significant change', or 'significant improvement'.

The threshold may be defined in terms of the standard deviation of the mental condition data for this user, or across multiple users, in the absence of any treatment. (e.g. a positive effect of 3 standard deviations may be considered significant, for example).

Additionally, apparatus 2000 may be configured to analyze treatment effectiveness across a network of users, where treatment effectiveness may be calculated statistically for various user groups with sets of shared user properties.

In this manner, apparatus 2000 can determine whether a treatment (such as a treatment plan) is effective at treatment of a mental condition of the user.

Example System

Embodiments of the disclosure may further be implemented as a part of a system for determining the state of the mental condition of the user.

Figure 8:
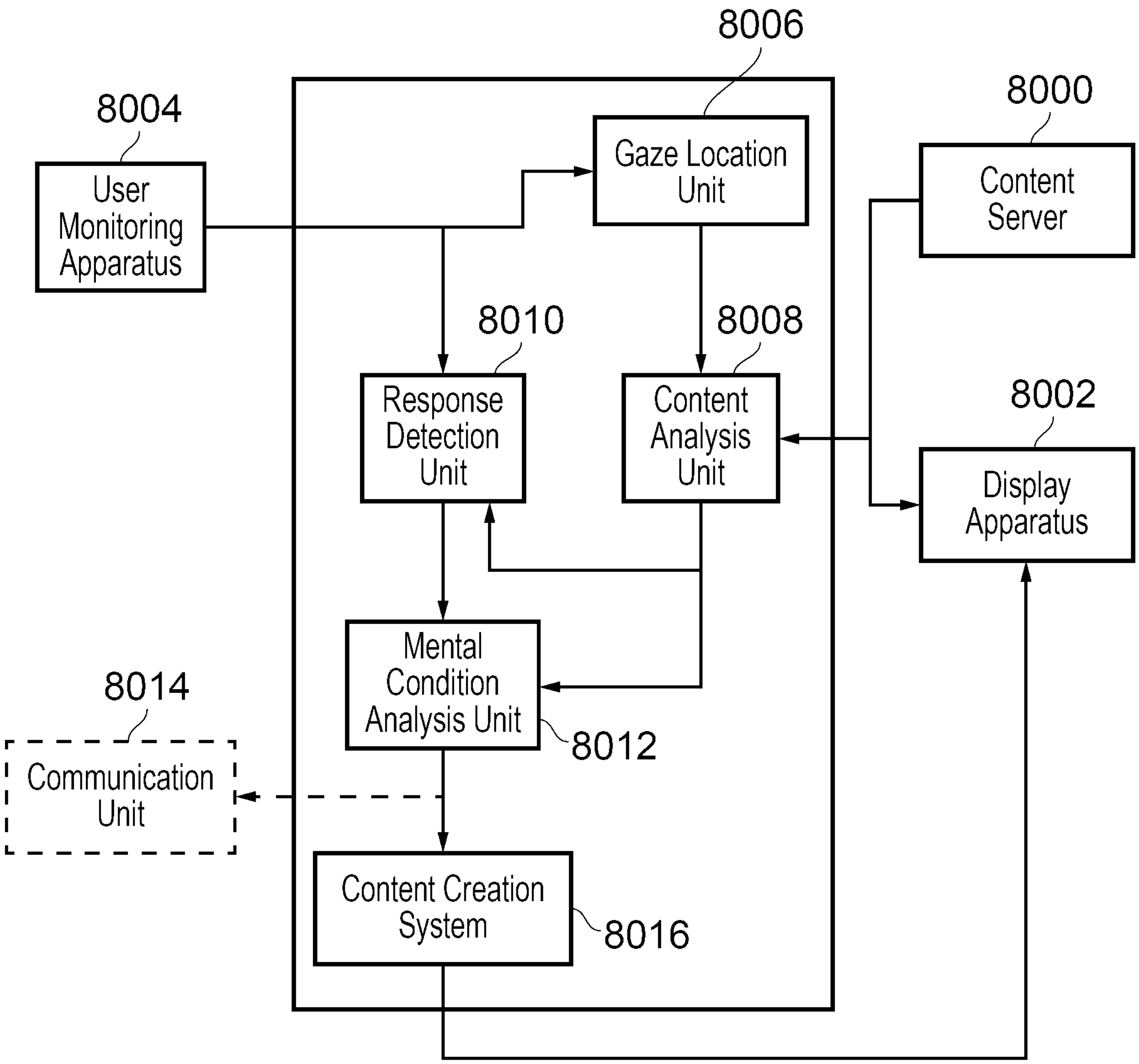
FIG. 8 illustrates an example process flow for the system in accordance with embodiments of the disclosure.

FIG. 8 illustrates an example system in accordance with embodiments of the disclosure.

The example system of FIG. 8 of the present disclosure comprises a server 8000 (The "Content Server") to store visual media which may also include or not include an audio component, such as a TV show episode, YouTube video, game, still image or other (The "Content Items") in a database which may be accessible to the user for downloading and viewing.

A display device 8002 ("Display Apparatus") to display Content Items to the user may also be provided in the system, where the display is capable of delivering stimuli in both peripheral and central regions of a user's vision. The display may, optionally, extend to a range of 6 degrees from a central point, and further, a 12 degree angle when measured from the user's viewing distance.

A user monitoring device 8004 ("User Monitoring Apparatus") to collect data relating to the user's response to the Image Data. In examples, the User Monitoring Apparatus may record a visual image of the user's face and eyes (The "User Monitoring Data"). The User Monitoring Apparatus may therefore consist of a self-facing camera contained within a head mounted display, or mounted near to a computer monitor.

The system further comprises processing circuitry configured to perform functions. This processing circuitry may be located as a cloud server or locally to the user such as a games console or other local computing device.

The processing circuitry may include a gaze location unit 8006 (the "Gaze Location Unit") to determine the user's gaze location within the spatial coordinates of the Image Data (The "Gaze Location Data") from the User Monitoring Data and known functions of the Display Apparatus. The processing circuitry may further include a content analysis unit 8008 (the "Content Analysis Unit") to determine the properties of visual stimuli occurring within the Image Data (The "Visual Stimulus Properties").

Processing circuitry of the system may further include a response detection unit 8010 (the "Response Detection Unit") to determine the user's autonomic response to the Emotionally Salient Stimuli by processing the User Monitoring Data. This User Monitoring Data can then be used by a Mental Condition Analysis Unit 8012 to determine the state of the mental condition of the user.

Optionally, the example system may further include a communication unit 8014 and a content creation system 8016.

Figure 7:
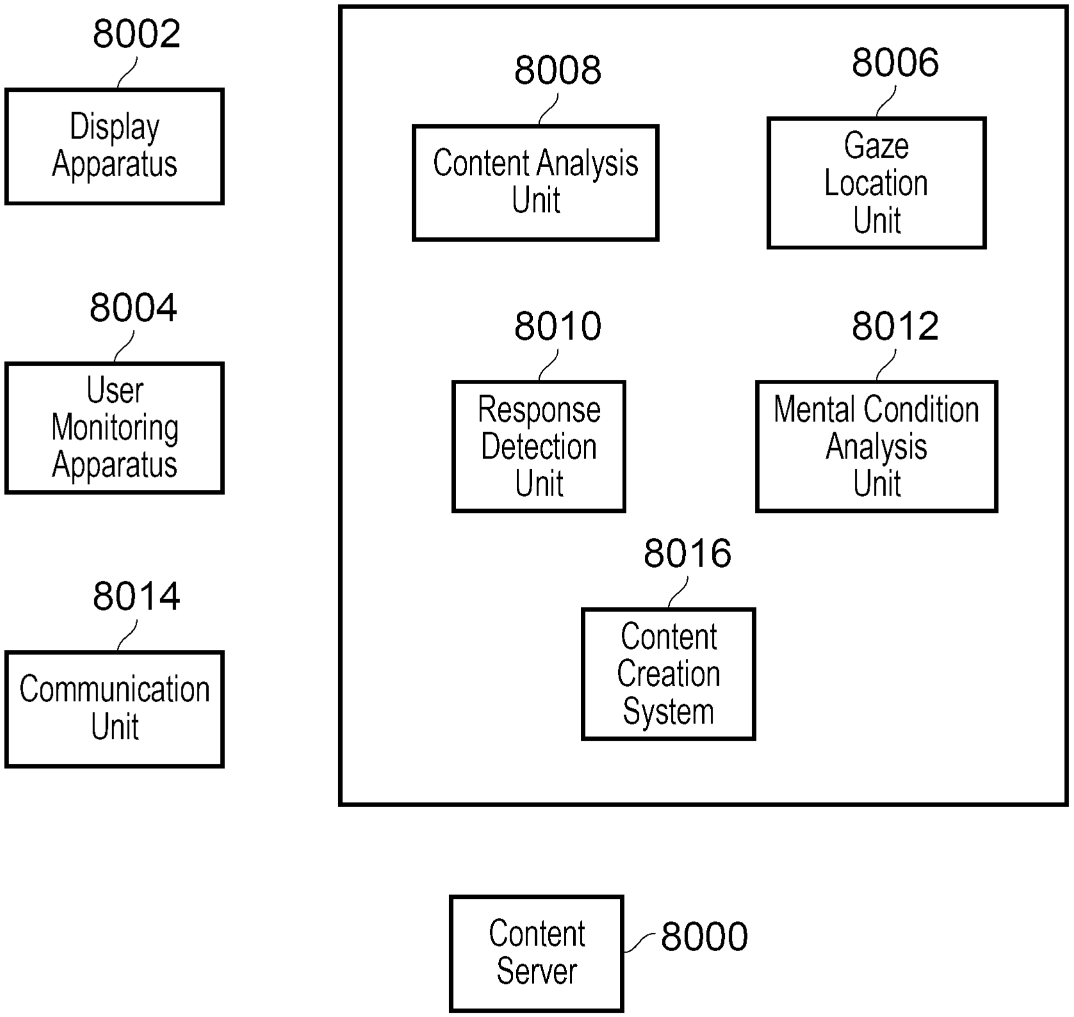
FIG. 7 illustrates an example system in accordance with embodiments of the disclosure.

The example system of FIG. 7 of the present disclosure can therefore be used in order to determine a state of a mental condition of the user.

FIG. 8 illustrates an example process flow for determining the state of a mental condition of a user using the system of FIG. 7. The individual method steps of the process are illustrated in FIG. 9 of the present disclosure.

In this example, a user places the Display Apparatus on their face such that they can view images which are displayed by the display apparatus (in this example, the display device is a wearable display device such as a head-mounted display or the like). Then, the user selects certain content (Content Items) to view from the Content Server. Content Items are then transmitted from a Content Server, such as a cloud server to the Display Apparatus and received by the processing circuitry (this corresponds to step S9000 of FIG. 9 of the present disclosure).

Figure 9:
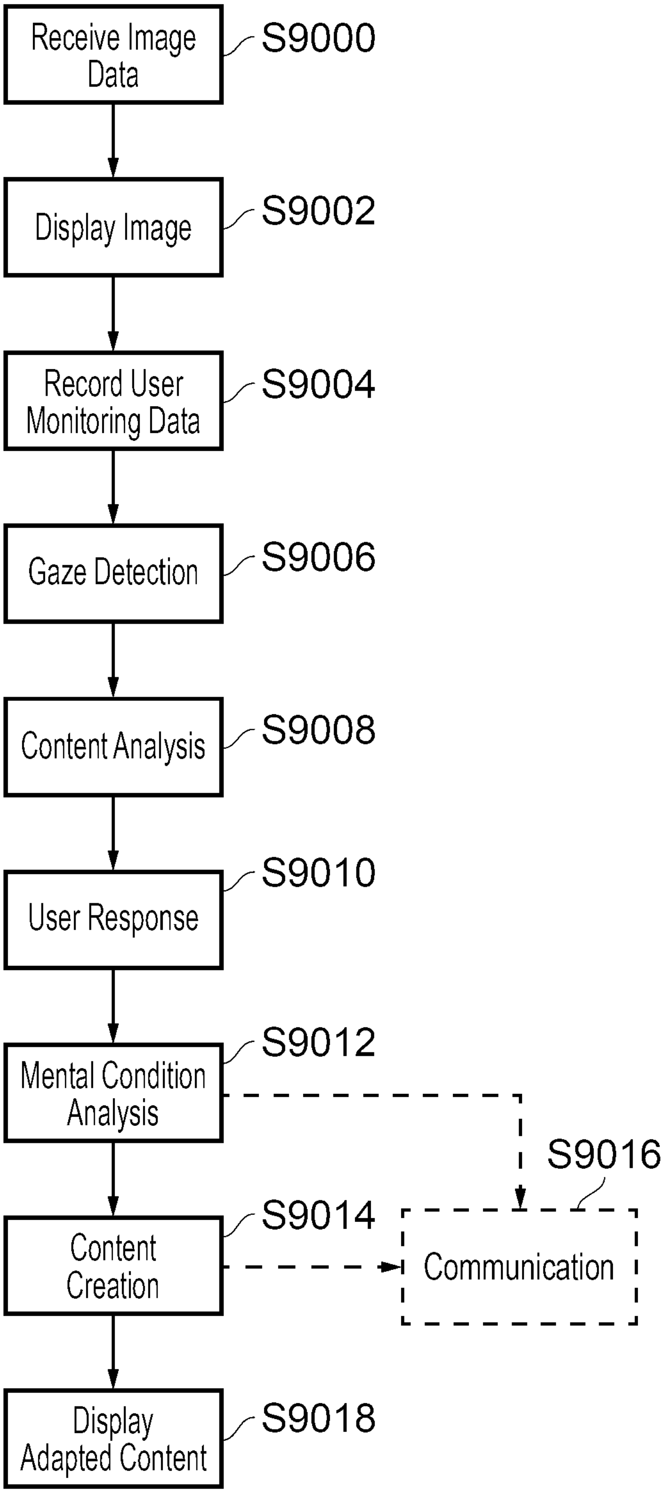
FIG. 9 illustrates an example method in accordance with embodiments of the disclosure.

The Display Apparatus then displays Image Data to the user (this corresponds to step S9002 of FIG. 9).

As the content is displayed to the user, the user will respond to the display of the first image. That is, when emotive content is displayed to the user (e.g. certain visual features) the user will undergo a physiological response. As such, the User Monitoring Apparatus records User Monitoring Data. This may include data inactive in a change of the dilation of the user's pupils for example. This corresponds to step S9004 of FIG. 9 of the present disclosure.

In order to determine the state of the mental condition of the user, differentiation between the response of the user to features which are displayed in different image regions must be assessed (e.g. whether the feature is presented in the central or peripheral vision of the user). Therefore, the Gaze Detection Unit is configured to determine where in the image data displayed by the Display Apparatus the user is looking. This corresponds to the method step S9006 of FIG. 9 of the present disclosure.

The Content Items from the Content Server are received also by the Content Analysis Unit. The Content Analysis Unit then analyses the Content Items in order to determine the properties of visual stimuli within the Content Items. As such, regardless of the content which the user chooses to receive from the Content Server, the content can be used in order to determine the state of the mental condition of the user, since the properties of the image can be analysed by the processing circuitry (and need not be known in advance). This corresponds to step S9008 of FIG. 9 of the present disclosure.

Then, the Response Detection Unit detects autonomic responses which occur in response to visual stimuli. For example, when visual stimuli are detected by the Content Analysis Unit, the User Monitoring Data occurring in a predetermined period following the display of the visual stimuli can be analysed by the Response Detection Unit in order to determine the autonomic response of the user (e.g. increase in dilation of the user's pupils) which occurs subsequently to the display of the visual stimuli. This corresponds to Step S9010 of FIG. 9 of the present disclosure.

The properties of the visual stimuli determined by the Content Analysis Unit ("Visual Stimulus Properties) and the user response date ("Physiological Response Data") can then be passed to the Mental Condition Analysis Unit. The Mental Condition Analysis unit is then configured to use this information in order to determine the state of the mental condition of the user. For example, the Mental Condition Analysis Unit may calculate the user's Mental Condition Data by inputting the Physiological Response Data and Visual Stimulus Properties a trained neural network for determination of the state of the mental condition of the user. This corresponds to step S9012 of FIG. 9 of the present disclosure.

In step S9014 of FIG. 9 of the present disclosure, the Content Creation System creates an Adapted Content which has advantageous condition testing properties, for example. This Adapted Content is created in view of the determined state of the mental condition of the user as indicated in the Mental Condition Data received from the Mental Condition Analysis Unit. The Adapted Content is then passed from the Content Creation System to the Display Apparatus for display to the user in step S9016 of FIG. 9 of the present disclosure.

Optionally, the Mental Condition Data (indicating the state of the user's mental condition) can then be passed to the Communication Unit for communication to an end user (e.g. a healthcare professional or the like). This corresponds to step S9018 of FIG. 9 of the present disclosure.

Accordingly, in this manner, the system can determine the state of the user's mental condition.

Of course, it will be appreciated that while a specific example implementation of a system for determining the state of the user's mental condition is provided with reference to FIGS. 7 to 9 of the present disclosure, the present disclosure is not particularly limited in this regard. The scope of the present disclosure is defined in accordance with the appended claims.

Figure 10:
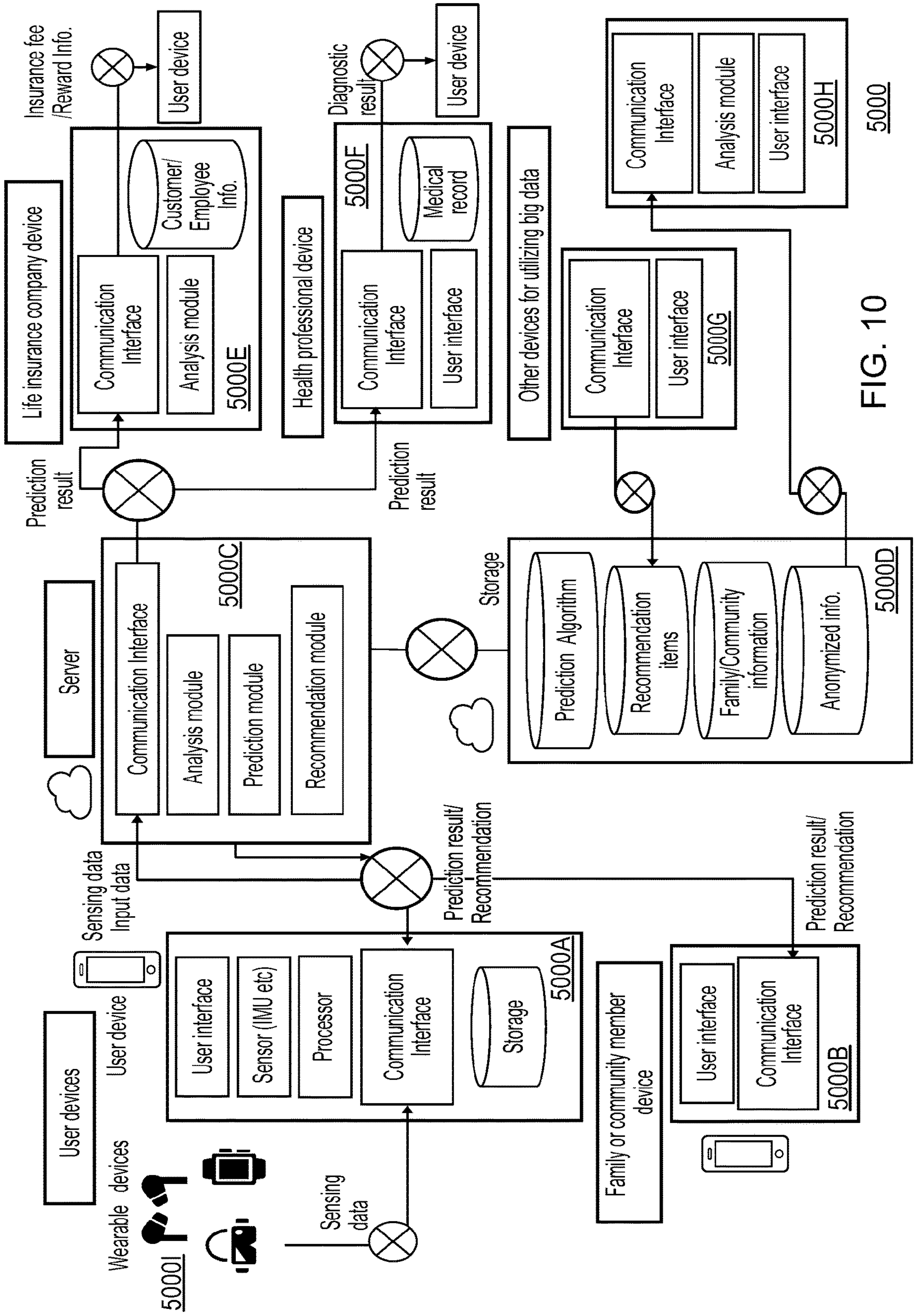
FIG. 10 illustrates an example system in accordance with embodiments of the disclosure.

Furthermore, although the foregoing has been described with reference to embodiments being carried out on a device or various devices (such as apparatus 2000 described with reference to FIG. 2 of the present disclosure) it will be appreciated that the disclosure is not so limited. In embodiments, the disclosure may be carried out on a system 5000 such as that shown in FIG. 10. That is, FIG. 10 illustrates an example system in accordance with embodiments of the disclosure which can be used in order to determine the state of a user's mental condition.

In the system 5000, the wearable devices 50001 are devices that are worn on a user's body. For example, the wearable devices may be earphones, a smart watch, Virtual Reality Headset or the like. The wearable devices contain or are connected to sensors that measure the movement of the user and which create sensing data to define the movement or position of the user. Sensing data may include, for example, information which can be used in order to determine the gaze direction of the user. This sensing data is provided over a wired or wireless connection to a user device 5000A. Of course, the disclosure is not so limited. In embodiments, the sensing data may be provided directly over an internet connection to a remote device such as a server 5000C located on the cloud. In further embodiments, the sensing data may be provided to the user device 5000A and the user device 5000A may provide this sensing data to the server 5000C after processing the sensing data. In the embodiments shown in FIG. 10, the sensing data is provided to a communication interface within the user device 5000A. The communication interface may communicate with the wearable device(s) using a wireless protocol such as low power Bluetooth or WiFi or the like.

The user device 5000A is, in embodiments, a mobile phone or tablet computer. The user device 5000A has a user interface which displays information and icons to the user. Within the user device 5000A are various sensors such as gyroscopes and accelerometers that measure the position and movement of a user. The operation of the user device 5000A is controlled by a processor which itself is controlled by computer software that is stored on storage. Other user specific information such as profile information is stored within the storage for use within the user device 5000A. As noted above, the user device 5000A also includes a communication interface that is configured to, in embodiments, communicate with the wearable devices. Moreover, the communication interface is configured to communicate with the server 5000C over a network such as the Internet. In embodiments, the user device 5000A is also configured to communicate with a further device 5000B. This further device 5000B may be owned or operated by a family member or a community member such as a carer for the user or a medical practitioner or the like. This is especially the case where the user device 5000A is configured to provide a prediction result and/or recommendation for the user. For example, in some situations the result of a determination of a state of the user's mental condition could be provided to the user (or a medical practitioner or the like). The disclosure is not so limited and in embodiments, the prediction result and/or recommendation for the user may be provided by the server 5000C.

The further device 5000B has a user interface that allows the family member or the community member to view the information or icons. In embodiments, this user interface may provide information relating to the user of the user device 5000B such as diagnosis, recommendation information or a prediction result for the user. This information relating to the user of the user device 5000B is provided to the further device 5000B via the communication interface and is provided in embodiments from the server 5000C or the user device 5000A or a combination of the server 5000C and the user device 5000A.

The user device 5000A and/or the further device 5000B are connected to the server 5000C. In particular, the user device 5000A and/or the further device 5000B are connected to a communication interface within the server 5000C. The sensing data provided from the wearable devices and or the user device 5000A are provided to the server 5000C. Other input data such as user information or demographic data is also provided to the server 5000C. The sensing data is, in embodiments, provided to an analysis module which analyses the sensing data and/or the input data. This analysed sensing data is provided to a prediction module that predicts the likelihood of the user of the user device having a condition now or in the future and in some instances, the severity of the condition (e.g. a prediction of the severity of a user's level of depression or anxiety). The predicted likelihood is provided to a recommendation module that provides a recommendation to the user and/or the family or community member. Although the prediction module is described as providing the predicted likelihood to the recommendation module, the disclosure is not so limited and the predicted likelihood may be provided directly to the user device 5000A and/or the further device 5000B.

Additionally, connected to or in communication with the server 5000C is storage 5000D. The storage 5000D provides the prediction algorithm that is used by the prediction module within the server 5000C to generate the predicted likelihood. Moreover, the storage 5000D includes recommendation items that are used by the recommendation module to generate the recommendation to the user. The storage 5000D also includes in embodiments family and/or community information. The family and/or community information provides information pertaining to the family and/or community member such as contact information for the further device 5000B.

Also provided in the storage 5000D is an anonymised information algorithm that anonymises the sensing data. This ensures that any sensitive data associated with the user of the user device 5000A is anonymised for security. The anonymised sensing data is provided to one or more other devices which is exemplified in FIG. 10 by device 5000H. This anonymised data is sent to the other device 5000H via a communication interface located within the other device 5000H. The anonymised data is analysed with the other data 5000H by an analysis module to determine any patterns from a large number set of sensing data. This analysis will improve the recommendations made by the recommendations module and will improve the predictions made from the sensing data. Similarly, a second other device 5000G is provided that communicates with the storage 5000D using a communication interface.

Returning now to server 5000C, as noted above, the prediction result and/or the recommendation generated by the server 5000C is sent to the user device 5000A and/or the further device 5000B.

Although the prediction result is used in embodiments to assist the user or his or her family member or community member, the prediction result may be also used to provide more accurate health assessments for the user. This will assist in purchasing products such as life or health insurance or will assist a health professional. This will now be explained.

The prediction result generated by server 5000C is sent to the life insurance company device 5000E and/or a health professional device 5000F. The prediction result is passed to a communication interface provided in the life insurance company device 5000E and/or a communication interface provided in the health professional device 5000F. In the event that the prediction result is sent to the life insurance company device 5000E, an analysis module is used in conjunction with the customer information such as demographic information to establish an appropriate premium for the user. In instances, rather than a life insurance company, the device 5000E could be a company's human resources department and the prediction result may be used to assess the health of the employee. In this case, the analysis module may be used to provide a reward to the employee if they achieve certain health parameters. For example, if the user has a lower prediction of ill health, they may receive a financial bonus. This reward incentivises healthy living. Information relating to the insurance premium or the reward is passed to the user device.

In the event that the prediction result is passed to the health professional device 5000F, a communication interface within the health professional device 5000F receives the prediction result. The prediction result is compared with the medical record of the user stored within the health professional device 5000F and a diagnostic result is generated. The diagnostic result provides the user with a diagnosis of a medical condition determined based on the user's medical record and the diagnostic result is sent to the user device.

Of course, it will be appreciated that the present disclosure is not particularly limited to this specific example system.

Furthermore, embodiments of the present disclosure are defined by the following numbered clauses:

(1)

An information processing system, the information processing apparatus comprising circuitry configured to:

control a display device to display a first image to a user;

detect a gaze location of the user corresponding to a portion of the first image observed by the user;

acquire one or more content properties of the first image displayed to the user based on an analysis of the first image;

acquire user response data relating to the user's autonomic response to the display of the first image; and determine a state of the user's mental condition based on the user response data, the one or more content properties of the first image and the gaze location of the user, wherein the mental condition includes at least one of anxiety and/or depression.

(2)

The information processing system according to (1), wherein the circuitry is further configured to generate a second image for display to the user, the second image being generated in accordance with the determined state of the user's mental condition.

(3)

The information processing system according to any preceding clause, wherein the circuitry is further configured to acquire the first image from a content server.

(4)

The information processing system according to any preceding clause, further comprising the display device and wherein the display device is one of at least a virtual reality display, an augmented reality display or a widescreen display screen.

(5)

The information processing system according to any preceding clause, wherein the circuitry is further configured to detect a gaze location of the user using an eye tracking device.

(6)

The information processing system according to (5), further comprising the eye tracking device, wherein the eye-tracking device comprises eye-facing cameras.

(7)

The information processing system according to any preceding clause, wherein the circuitry is further configured to analyze the first image in order to acquire the one or more content properties of the first image.

(8)

The information processing system according to (7), wherein the circuitry is further configured to analyze the one or more content properties of the first image based on at least one of pixel colour, pixel brightness, object recognition, properties of the image scene and/or image metadata.

(9)

The information processing system according to (1), (7) or (8), wherein the one or more content properties of the first image are the location of emotional stimuli within the first image.

(10)

The information processing system according to (9), wherein the circuitry is further configured to use the location of the emotional stimuli within the first image and the gaze direction of the user to determine whether the emotional stimuli within the first image are within the central vision or peripheral vision of the user; and determine the state of the user's mental condition based on whether the emotional stimuli within the first image are within the central vision or peripheral vision of the user and the user response data.

(11)

The information processing system according to (10), wherein the circuity is further configured to differentiate between a mental condition of anxiety and depression by comparing the user response data for emotional stimuli in the central vision and emotional stimuli in the peripheral vision of the user.

(12)

The information processing system according to any preceding clause, wherein the user response data comprises at least one of information relating to pupillary diameter, pupillary saccadic motion, facial expression, skin conductance, facial blood flow, heart rate and/or skin temperature.

(13)

The information processing system according to any preceding clause, the information processing apparatus further comprising one or more detecting devices configured to detect the user response data.

(14)

The information processing system according to any preceding clause, wherein the circuitry is further configured to determine the state of the user's mental condition using a trained model.

(15)

The information processing system according to (14), wherein the circuitry is further configured to adapt the first image by adapting the one or more content properties of the first image.

(16)

The information processing system according to any preceding clause, wherein the circuitry is further configured to generate the second image for display to the user by adapting the first image in accordance with the determined state of the user's mental condition.

(17)

The information processing system according to any preceding clause, wherein the circuitry is further configured to generate the second image data for display to the user by acquiring the second image data from a content server in accordance with the determined state of the user's mental condition.

(18)

The information processing system according to any preceding clause, wherein the circuitry is further configured to generate feedback in accordance with the determined state of the user's mental condition.

(19)

An information processing system, the information processing apparatus comprising circuitry configured to:

detect a gaze location of a user corresponding to a portion of an image observed by the user on a display device;

acquire one or more content properties of the first image displayed to the user based on an analysis of the first image;

acquire user response data relating to the user's autonomic response to the display of the image; and determine a state of the user's mental condition based on the user response data, the one or more content properties of the image and the gaze location of the user, wherein the mental condition includes at least one of anxiety and/or depression.

(20)

An information processing system, the information processing apparatus comprising circuitry configured to:

determine a state of a user's mental condition based on user response data relating to a user's autonomic response to display of an image, one or more content properties of the image and a gaze location of the user corresponding to a portion of the image observed by the user; and generate a second image for display to the user, the second image being generated in accordance with the determined state of the user's mental condition.

(21)

An information processing system, the information processing apparatus comprising circuitry configured to:

control a display device to display an image to a user;

detect a gaze location of the user corresponding to a portion of the image observed by the user;

acquire one or more content properties of the first image displayed to the user based on an analysis of the first image; and acquire user response data relating to the user's autonomic response to the display of the image.

(22)

An information processing method comprising:

controlling a display device to display a first image to a user;

detecting a gaze location of the user corresponding to a portion of the first image observed by the user;

acquiring one or more content properties of the first image displayed to the user based on an analysis of the first image;

acquiring user response data relating to the user's autonomic response to the display of the first image; and determining a state of the user's mental condition based on the user response data, the one or more content properties of the first image and the gaze location of the user, wherein the mental condition includes at least one of anxiety and/or depression.

(23)

An information processing method comprising:

detecting a gaze location of a user corresponding to a portion of an image observed by the user on a display device;

acquiring one or more content properties of the first image displayed to the user based on an analysis of the first image;

acquiring user response data relating to the user's autonomic response to the display of the image; and determining a state of the user's mental condition based on the user response data, the one or more content properties of the image and the gaze location of the user, wherein the mental condition includes at least one of anxiety and/or depression.

(24)

An information processing method comprising:

determining a state of a user's mental condition based on user response data relating to a user's autonomic response to display of an image, one or more content properties of the image and a gaze location of the user corresponding to a portion of the image observed by the user; and generating a second image for display to the user, the second image being generated in accordance with the determined state of the user's mental condition.

(25)

An information processing method comprising:

controlling a display device to display an image to a user;

detecting a gaze location of the user corresponding to a portion of the image observed by the user;

acquiring one or more content properties of the first image displayed to the user based on an analysis of the first image; and acquiring user response data relating to the user's autonomic response to the display of the image.

(26)

Computer program product comprising instructions which, when implemented by a computer, cause the computer to perform a method according to any of (22) to (25).

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

The invention claimed is:

1. An information processing system comprising circuitry configured to:

control a display device to display a first image to a user;

detect a gaze location of the user corresponding to a portion of the first image observed by the user;

acquire one or more content properties of the first image displayed to the user based on an analysis of the first image, wherein the one or more content properties of the first image are a location of emotional stimuli within the first image;

acquire user response data relating to the user's autonomic response to the display of the first image; and determine a state of the user's mental condition based on the user response data, the one or more content properties of the first image and the gaze location of the user, wherein the mental condition includes at least one of anxiety and/or depression, wherein the circuitry is further configured to:

use the location of the emotional stimuli within the first image and the gaze location of the user to determine whether the emotional stimuli within the first image are within a central vision or peripheral vision of the user; and determine the state of the user's mental condition based on whether the emotional stimuli within the first image are within the central vision or peripheral vision of the user and the user response data.

2. The information processing system according to claim 1, wherein the circuitry is further configured to generate a second image for display to the user, the second image being generated in accordance with the determined state of the user's mental condition.

3. The information processing system according to claim 1, wherein the circuitry is further configured to acquire the first image from a content server.

4. The information processing system according to claim 1, further comprising the display device and wherein the display device is one of at least a virtual reality display, an augmented reality display or a widescreen display screen.

5. The information processing system according to claim 1, wherein the circuitry is further configured to detect a gaze location of the user using an eye-tracking device.

6. The information processing system according to claim 5, further comprising the eye-tracking device, wherein the eye-tracking device comprises eye-facing cameras.

7. The information processing system according to claim 1, wherein the circuitry is further configured to analyze the first image in order to acquire the one or more content properties of the first image.

8. The information processing system according to claim 7, wherein the circuitry is further configured to analyze the one or more content properties of the first image based on at least one of pixel colour, pixel brightness, object recognition, properties of an image scene and/or image metadata.

9. The information processing system according to claim 1, wherein the circuitry is further configured to differentiate between a mental condition of anxiety and depression by comparing the user response data for emotional stimuli in the central vision and emotional stimuli in the peripheral vision of the user.

10. The information processing system according to claim 1, wherein the user response data comprises at least one of information relating to pupillary diameter, pupillary saccadic motion, facial expression, skin conductance, facial blood flow, heart rate and/or skin temperature.

11. The information processing system according to claim 1, comprising one or more detecting devices configured to detect the user response data.

12. The information processing system according to claim 1, wherein the circuitry is further configured to determine the state of the user's mental condition using a trained model.

13. The information processing system according to claim 12, wherein the circuitry is further configured to adapt the first image by adapting the one or more content properties of the first image.

14. The information processing system according to claim 1, wherein the circuitry is further configured to generate a second image for display to the user by adapting the first image in accordance with the determined state of the user's mental condition.

15. The information processing system according to claim 1, wherein the circuitry is further configured to generate second image data for display to the user by acquiring the second image data from a content server in accordance with the determined state of the user's mental condition.

16. The information processing system according to claim 1, wherein the circuitry is further configured to generate feedback in accordance with the determined state of the user's mental condition.

17. An information processing system comprising circuitry configured to:

detect a gaze location of a user corresponding to a portion of an image observed by the user on a display device;

acquire one or more content properties of a first image displayed to the user based on an analysis of the first image, wherein the one or more content properties of the first image are a location of emotional stimuli within the first image;

acquire user response data relating to the user's autonomic response to the display of the image; and determine a state of the user's mental condition based on the user response data, the one or more content properties of the image and the gaze location of the user, wherein the mental condition includes at least one of anxiety and/or depression, wherein the circuitry is further configured to:

use the location of the emotional stimuli within the first image and the gaze location of the user to determine whether the emotional stimuli within the first image are within a central vision or peripheral vision of the user; and determine the state of the user's mental condition based on whether the emotional stimuli within the first image are within the central vision or peripheral vision of the user and the user response data.

18. An information processing system comprising circuitry configured to:

determine a state of a user's mental condition based on user response data relating to a user's autonomic response to display of an image, one or more content properties of the image, the one or more content properties of the image being a location of emotional stimuli within the image, and a gaze location of the user corresponding to a portion of the image observed by the user; and generate a second image for display to the user, the second image being generated in accordance with the determined state of the user's mental condition, wherein the circuitry is further configured to:

use the location of the emotional stimuli within the image and the gaze location of the user to determine whether the emotional stimuli within the image are within a central vision or peripheral vision of the user; and determine the state of the user's mental condition based on whether the emotional stimuli within the image are within the central vision or peripheral vision of the user and the user response data.

19. An information processing system comprising circuitry configured to:

control a display device to display an image to a user;

detect a gaze location of the user corresponding to a portion of the image observed by the user;

acquire one or more content properties of the image displayed to the user based on an analysis of the image, wherein the one or more content properties of the image are a location of emotional stimuli within the image; and acquire user response data relating to the user's autonomic response to the display of the image, wherein the circuitry is further configured to:

use the location of the emotional stimuli within the image and the gaze location of the user to determine whether the emotional stimuli within the image are within a central vision or peripheral vision of the user; and determine a state of the user's mental condition based on whether the emotional stimuli within the image are within the central vision or peripheral vision of the user and the user response data.

20. An information processing method comprising:

controlling a display device to display a first image to a user;

detecting a gaze location of the user corresponding to a portion of the first image observed by the user;

acquiring one or more content properties of the first image displayed to the user based on an analysis of the first image, wherein the one or more content properties of the first image are a location of emotional stimuli within the first image;

acquiring user response data relating to the user's autonomic response to the display of the first image; and determining a state of the user's mental condition based on the user response data, the one or more content properties of the first image and the gaze location of the user, wherein the mental condition includes at least one of anxiety and/or depression, wherein the method further comprises:

using the location of the emotional stimuli within the first image and the gaze location of the user to determine whether the emotional stimuli within the first image are within a central vision or peripheral vision of the user; and wherein determining the state of the user's mental condition is based on whether the emotional stimuli within the first image are within the central vision or peripheral vision of the user and the user response data.

21. Computer program product comprising instructions which, when implemented by a computer, cause the computer to perform a method according to claim 20.

22. An information processing method comprising:

detecting a gaze location of a user corresponding to a portion of an image observed by the user on a display device;

acquiring one or more content properties of the image displayed to the user based on an analysis of the image, wherein the one or more content properties of the image are a location of emotional stimuli within the image;

acquiring user response data relating to the user's autonomic response to the display of the image; and determining a state of the user's mental condition based on the user response data, the one or more content properties of the image and the gaze location of the user, wherein the mental condition includes at least one of anxiety and/or depression, wherein the method further comprises:

using the location of the emotional stimuli within the image and the gaze location of the user to determine whether the emotional stimuli within the image are within a central vision or peripheral vision of the user; and wherein determining the state of the user's mental condition is based on whether the emotional stimuli within the image are within the central vision or peripheral vision of the user and the user response data.

23. Computer program product comprising instructions which, when implemented by a computer, cause the computer to perform a method according to claim 22.

24. An information processing method comprising:

determining a state of a user's mental condition based on user response data relating to a user's autonomic response to display of an image, one or more content properties of the image, the one or more content properties of the image being a location of emotional stimuli within the image, and a gaze location of the user corresponding to a portion of the image observed by the user; and generating a second image for display to the user, the second image being generated in accordance with the determined state of the user's mental condition, wherein the method further comprises:

using the location of the emotional stimuli within the image and the gaze location of the user to determine whether the emotional stimuli within the image are within a central vision or peripheral vision of the user; and determining a state of the user's mental condition based on whether the emotional stimuli within the image are within the central vision or peripheral vision of the user and the user response data.

25. Computer program product comprising instructions which, when implemented by a computer, cause the computer to perform a method according to claim 24.

26. An information processing method comprising:

controlling a display device to display an image to a user;

detecting a gaze location of the user corresponding to a portion of the image observed by the user;

acquiring one or more content properties of the image displayed to the user based on an analysis of the image, wherein the one or more content properties of the image are a location of emotional stimuli within the image; and acquiring user response data relating to the user's autonomic response to the display of the image, wherein the method further comprises:

using the location of the emotional stimuli within the image and the gaze location of the user to determine whether the emotional stimuli within the image are within a central vision or peripheral vision of the user; and wherein determining a state of the user's mental condition is based on whether the emotional stimuli within the image are within the central vision or peripheral vision of the user and the user response data.

27. Computer program product comprising instructions which, when implemented by a computer, cause the computer to perform a method according to claim 26.

* * * * *